(12) United States Patent
Gerritsen et al.

(10) Patent No.: US 7,332,579 B2
(45) Date of Patent: Feb. 19, 2008

(54) ANTIBODIES TO HUMAN ERBB4

(75) Inventors: Mary E. Gerritsen, San Mateo, CA (US); Mark X. Sliwkowski, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 310 days.

(21) Appl. No.: 10/362,380

(22) PCT Filed: Aug. 29, 2001

(86) PCT No.: PCT/US01/26984

§ 371 (c)(1),
(2), (4) Date: Aug. 6, 2003

(87) PCT Pub. No.: WO02/18444

PCT Pub. Date: Mar. 7, 2002

(65) Prior Publication Data
US 2004/0052786 A1 Mar. 18, 2004

Related U.S. Application Data

(63) Continuation of application No. 09/940,101, filed on Aug. 27, 2001, now abandoned.

(60) Provisional application No. 60/229,679, filed on Sep. 1, 2000, provisional application No. 60/265,516, filed on Jan. 31, 2001.

(51) Int. Cl.
C07K 16/00 (2006.01)
C07K 16/18 (2006.01)
C07K 16/28 (2006.01)
C12P 21/08 (2006.01)

(52) U.S. Cl. .............. 530/387.1; 530/387.3; 530/388.1; 530/388.22

(58) Field of Classification Search ............ 530/387.1, 530/387.3, 388.22, 388.1
See application file for complete search history.

(56) References Cited

U.S. PATENT DOCUMENTS

| | | | |
|---|---|---|---|
| 4,968,603 | A | 11/1990 | Slamon et al. |
| 5,183,884 | A | 2/1993 | Kraus et al. |
| 5,641,869 | A | 6/1997 | Vandler et al. |
| 5,811,098 | A | 9/1998 | Plowman et al. |
| 5,821,337 | A | 10/1998 | Carter et al. |
| 5,968,511 | A * | 10/1999 | Akita et al. ............ 424/141.1 |

FOREIGN PATENT DOCUMENTS

| | | |
|---|---|---|
| EP | 0 444 961 A1 | 9/1991 |
| EP | 0 599 274 A1 | 6/1994 |
| WO | WO 96 15128 | 5/1996 |
| WO | WO 99 02681 | 1/1999 |
| WO | WO 99 19488 | 4/1999 |
| WO | WO 00 31048 A | 6/2000 |

OTHER PUBLICATIONS

Ngo et al., 1994, The Protein Folding Problem and Tertiary Structure Prediction, pp. 491-495.*
Attwood et al, The Babel of Bioinformatics, 2000, Science vol. 290 No. 5491: 471-473.*
Skolnick et al., From genes to protein structure and function: novel applications of computational approaches in the genomic era, Jan. 2000, Trends in Biotech. 18(1): 34-39.*
Kuby et al, Immunology, Second edition, pp. 86-96, 1994.*
Abaza et al, J of Protein Chemistry 11(5): 433-444, 1992.*
Rudikoff et al, Proc Natl Acad Sci USA 79: 1979. 1982-83.*
Barrios et al, J Molecular Recognition 17: 332-338, 2004.*
Piatesi et al, ChemBioChem 5: 460-466, 2004.*
Lauder et al, "Quantification of the repair process involved in the repair of a cell monolayer using an in vitro model of mechanical injury," Angiogenesis 2(1):67-80, 1998.*
Poon et al., "Rapamycin Inhibits Smooth Muscle Cell Migration," J. Clin. Invest. 98:2277-2283 (1996).*
Wakino et al., "Retinoids Inhibit Proliferation of Human Coronary Smooth Muscle Cells by Modulating Cell Cycle Regulators," Arterioscler Thromb Vasc Biol 21:746-751 (2001).*
Mitzutani et al, Journal of Hypertension, 18:1833-1840, 2000.*
Hou et al, American Journal of Pathology, 1562:467-476, 2000.*
Hayashi et al, Hypertension, 35(2):237-243, 2000.*
Bianco et al. "Cripto-1 indirectly stimulates the tyrosine phosphorylation of erb B-4 through a novel receptor" *The Journal of Biological Chemistry* 274(13):8624-8629 (1999).
Chen et al. "An immunological approach reveals biological differences between the two NDF/heregulin receptors ErbB-3 and ErbB-4" *The Journal of Biological Chemistry* 271(13):7620-7629 (1996).
Topol et al. *JAMA* 278:479-484 (1997).
Menges et al. *Digestion* 65(3):184-189 (2002).
Krymskaya et al. *Am. J. Physiol.*276:L246-L255 (1999).
Andres, V., "Control of vascular smooth muscle cell growth and its implication in atherosclerosis and restenosis (Review)", *International Journal of Molecular Medicine*, 2:81-89 (1998).
Baselga, J. et al., "Phase II Study of Weekly Intravenous Recombinant Humanized Anti-p185 $^{HER2}$ Monoclonal Antibody in Patients With HER2/neu- Overexpressing Metastatic Breast Cancer" *Journal of Clinical Oncology*, 14(3):737-744 (1996).

(Continued)

Primary Examiner—Christina Chan
Assistant Examiner—Phuong Huynh
(74) Attorney, Agent, or Firm—Atulya R. Agarwal; Ginger R. Dreger, Esq.; Heller Ehrman LLP

(57) ABSTRACT

The present invention concerns isolated antibodies that specifically bind to the human ErbB4 of SEQ ID NO:2, as well as humanized antibodies, human antibodies and antibody fragments, as well as bispecific antibodies capable of binding both the human ErbB4 of SEQ ID NO:2 and ErbB3. The invention further concerns antibodies which specifically bind to human ErbB4 of SEQ ID NO: 2 with a Kd less than 100 nM, antibodies which specifically bind to human ErbB4 of SEQ ID NO: 2 and which reduces heregulin binding thereto, and antibodies which specifically bind to human ErbB4 of SEQ ID NO: 2 and which reduce heregulin-induced tyrosine phosphorylation thereof.

27 Claims, 10 Drawing Sheets

OTHER PUBLICATIONS

Borer, J. G. et al., "Heparin-Binding EGF-Like Growth Factor Expression Increases Selectively in Bladder Smooth Muscle in Response to Lower Urinary Tract Obstruction" *Laboratory Investigation*, 79(11):1335-1345 (1999).

Carraway, K. L., III et al., "A Neu Acquaintance for ErbB3 and ErbB4: A Role for Receptor Heterodimerization.in Growth Signaling" *Cell*, 78:5-8 (1994).

Carraway, K. L., III et al., "Neuregulin-2, a new ligand of ErbB3/ErbB4-receptor tyrosine kinases" *Nature* 387:512-516 (1997).

Casterella, P. J. M.D. et al., "Prevention of Coronary Restenosis" *Cardiology In Review* 7(4):219-231 (1999).

Cerutis, D. R. et al., "Lysophosphatidic acid and EGF stimulate mitogenesis in human airway smooth muscle cells" *Am. J. Physiol.* 273:L10-L15 (1997).

Chang, H. et al., "Ligands for ErbB-family receptors encoded by a neuregulin-like gene" *Nature* 387:509-511 (1997).

Cohen, M. D. et al., "TGF-β1 Modulates Human Airway Smooth-Muscle Cell Proliferation Induced by Mitogens," *Am. J. Respir. Cell Mol. Biol.* 16: 85-90 (1997).

Earp, H. S. et al., "Heterodimerization and functional interaction between EGF receptor family members: A new signaling paradigm with implications for breast cancer research" *Breast Cancer Research and Treatment* 35:115-132 (1995).

Ellenius, K. et al. "A Novel Juxtamembrane Domain Isoform of HER4/ErbB4," *The Journal of Biological Chemist* 272(42):26761-26766 (1997).

Elenius, K. et al., "Characterization of a naturally occuring ErbB4 isoform that does not bind or activate phosphatidyl inositol 3-kinase" *Oncogene* 18: 2607-2615 (1999).

Freeman, M. R. et al., "Heparin-binding EGF-like Growth Factor Is an Autocrine Growth Factor for Human Urothelial Cells and Is Synthesized by Epithelial and Smooth Muscle Cells in the Human Bladder" *J. Clin. Invest.* 99(5):1028-1036 (1997).

Friess, H. et al., "Enhanced erbB-3 Expression in Human Pancreatic Cancer Correlates with Tumor Progression" *Clinical Cancer Research* 1:1413-1420 (1995).

Gorman, C. M. et al., "Transient Production of Proteins Using an Adenovirus Transformed Cell Line" *DNA and Protein Engineering Techniques* 2(1):3-10 (1990).

Groenen, L. C. et al., "Structure-Function Relationships for the EGF/TGF-α Family of Mitogens" *Growth Factors* 11:235-257 (1994).

Guy, P. M. et al., "Insect cell-expressed p180$^{erbB3}$ possesses an impaired tyrosine kinase activity" *Proc. Natl. Acad. Sci. USA* 91:8132-8136 (1994).

Harari, D. et al., "Neuregulin-4i a novel growth factor that acts through the ErbB-4 receptor tyrosine kinase" *Oncogen* 18:2681-2689 (1999).

Holmes, W. E. et al., "Identification of Heregulin, a Specific Activator of p185$^{erbB2}$" *Science*, 256:1205-1210 (1992).

Huang, M. T. F. et al., "Intervening sequences increase efficiency of RNA 3' processing and accumulation of cytoplasmic RNA" *Nucleic Acids Research* 18(4):937-947 (1990).

Hudziak, R. M. et al., "p 185HER2 Monoclonal Antibody Has Antiproliferative Effects In Vitro and Sensitizes Human Breast Tumor cells to Tumor Necrosis Factor" *Molecular and Cellular Biology* 9(3):1165-1172(1989).

Kaefer, M. et al., "A Nontoxic Diphtheria Toxin Analogue Inhibits Neonatal Bladder Smooth Muscle Cell Proliferation" *The Journal of Urology* 163: 580-584 (2000).

Kalmes, A. et al., "Heparin blockade of thrombin-induced smooth muscle cell migration involves inhibition of epidermal growth factor (EGF) receptor transactivation by heparin-binding EGF-like growth factor" *Circ. Res.* 87(2):92-98 (2000).

Kim, Hong-Hee et al., "Epidermal Growth Factor-dependent Association of Phosphatidylinositol 3-Kinase with the erbB3 Gene Product" *The Journal of Biological Chemistry* 269(40):24747-24755 (1994).

Kraus, M. H. et al., "Demonstration of ligand-dependent signaling by the erbB-3 tyrosine kinase and its constitutive activation in human breast tumor cells" *Proc. Natl. Acad. Sci. USA* 90:2900-2904 (1993).

Kraus, M. H. et al., "Isolation and characterization of *ERBB3*, a third member of the ERBB / edpidermal growth factor receptor family: Evidence for overexpression in a subset of human mammary tumors" *Proc. Natl. Acad. Sci. USA* 86:9193-9197 (1989).

Kunkel, T. A., "Rapid and efficient site-specific mutagenesis without phenotypic selection" *Proc. Natl. Acad. Sci, USA* 82:488-492 (1985).

Lee, D. C. et al. "Transforming Growth Factor α Expression, Regulation, and Biological Activities" *Pharmacological Reviews* 47(1):51-85 (1995).

Lemke, G., "Neuregulins in Development" *Molecular and Cellular Neuroscience* 7:247-262 (1996).

Lemoine, N. R. et al., "Expression of the ERBB3 gene product in breast cancer" *Br. J. Cancer* 66:1116-1121 (1992).

Lemoine, N. R. et al., "The erbB-3 Gene in Human Pancreatic Cancer" *Journal of Pathology* 168:269-273 (1992).

Lewis, G. D. et al., "Growth Regulation of Human Breast and Ovarian Tumor Cells by Hereguiin: Evidence for the Requirement of ErbB2 as a Critical Component in Mediating Hregulin Responsiveness" *Cancer Research* 56:1457-1465 (1996).

Morrissey, T. K. et al., "Axon-induced mitogenesis of human Schwann cells involves heregulin and p185$^{erbB2}$" *Proc. Natl. Acad. Sci. USA* 92: 1431-1435 (1995).

Oue, T. et al., "Smooth Muscle Cell Hypertrophy versus Hyperplasia in Infantile Hypertrophic Pyloric Stenosis" *Pediatric Research* 45(6): 853-857 (1999).

Plowman, G. D. et aL, "Heregulin induces tyrosine phosphorylation of HER4/p180$^{erbB4}$" *Nature* 366:473-475 (1993).

Plowman, G. D et al., "Ligand-specific activation of HER4/P180$^{erbB4}$, a fourth member of the epidermal growth factor receptor family" *Proc. Natl. Acad. Sci. USA* 90:1746-1750 (1993).

Poiler, D. N. et al., "Production and Characterization of a Polyclonal Antibody to the c-erbB-3 Protein: Examination of c-erbB-3 Protein Expression in Adenocarconomas" *Journal of Pathology*, 168:275-280 (1992).

Rajkumar, T. et al., "Expression of the C-erbB-3 Protein in gastrointestinal Tract tumours Determined by Monoclonal Antibody" *Journal of Pathology* 170:271-278 (1993).

Rosanio, S. et al., "Prevention of restenosis after Percutaneous Coronary Interventions: The Medical Approach" *Thromb Haemost* 82:164-170 (1999).

Ross, R. et al., "Platelet-derived growth factor and its role in health and disease" *Phil. Trans. R. Soc. Lond.* B(327):155-169 (1990).

Sanidas, E. e. et al., "Expression of the c-erbB-3 Gene Product in Gastric Cancer" *Int. J. Cancer* 54:935-940 (1993).

Sartor, C. I. et al., "HER4 Mediates Ligand-Dependent Antiproliferative and Differentiation Responses in Human Breast Cancer Cells" *Molecular and Cellular Biology* 21(13):4265-4275 (2001).

Schaefer, G. eta., "γ-Heregulin: a novel heregulin isoform that is an autocrine growth factor for the human breast cancer cell line, MDA-MB-175" *Oncogene* 15:1385-1394 (1997).

Shima H. et al., "Increased Local Synthesis of Epidermal Growth Factors in Infantile Hypertrophic Pyloric Stenosis" *Pediatric Research* 47(2):201-207 (2000).

Slamon, D. J. et al., "Human Breast Cancer: Correlation of Relapse and Survival with Amplification of the HER-*2/neu* Oncogene" *Science* 235:177-182 (1987).

Slamon, D. J., "Studies of the HER-*2/neu* Proto-oncogene in Human Breast and Ovarian Cancer" *Science* 244:707-712 (1989).

Sliwkowski, M. X. et al., "Coexpression of *erb*B2 and *erb*B3 Proteins Reconstitutes a High Affinity Receptor for Heregulin" *The Journal of Biological Chemistry* 269(20):14661-14665 (1994).

Zhang, D. et al., "Neuregulin-3 (NRG3): A novel neural tissue-enriched protein that binds and activates ErbB4" *Proc. Natl. Acad. Sci. USA* 94:9562-9567 (1997).

De Pascalis, R. et al., "Grafting of 'abbreviated' complementarity-determining regions containing specificity-determining residues essential for ligand contact to engineer a less immunogenic humanized monoclonal antibody," *J. Immunol.* 169:3076-3084 (2002).

Padlan, E. A. et al., "Identification of specificity-determining residues in antibodies," *FASEB J.* 9:133-139 (1995).

Tamura, M. et al., "Structural correlates of an anticarcinoma antibody: Identification of specificity-determining residues (SDRs) and development of a minimally immunogenic antibody variant by retention of SDRs only," *J. Immunol.* 164:1432-1441 (2000).

* cited by examiner

```
   1 aattgtcagc acgggatctg agacttccaa aaaatgaagc cggcgacagg actttgggtc
  61 tggtgagcc ttctcgtggc ggcggggacc gtccagccca gcgattctca gtcagtgtgt
 121 gcaggaacgg agaataaact gagctctctc tctgacctgg aacagcagta ccgagccttg
 181 cgcaagtact atgaaaaactg tgaggttgtc atgggcaacc tggagataac cagcattgag
 241 cacaaccggg acctctcctt ctgcggtct gttcgagaag tcacaggcta cgtgttagtg
 301 gctcttaatc agtttcgtta cctgcctctg gagaatttac gcattattcg tgggacaaaa
 361 ctttatgagg atcgatatgc cttggcaata tttttaaact acagaaaaga tggaaacttt
 421 ggacttcaag aacttgatt aaagaacttg acagaaatcc taaatggtgg agtctatgta
 481 gaccagaaca aattccttg ttatgcagac accattcatt ggcaagatat tgttcggaac
 541 ccatgcctt ccaacttgac tcttgtgtca acaaatggta gtcaggatg tggacgttgc
 601 cataagtcct gtactgccg ttgctgggga cccacagaaa atcattgcca gactttgaca
 661 aggacggtgt gtgcagaaca atgtgacggc agtgctacgt gacttacgt cagtgactgc
 721 tgccatcgag aatgtgctgg aggctgctca ggacctaagg acacagactg ctttgcctgc
 781 atgaatttca atgacagtgg agcatgtgtt actcagtgtc cccaacctt tgtctacaat
 841 ccaaccacct ttcaactgga gcacaatttc aatgcaaagt acacatatgg agcattctgt
 901 gtcaagaaat gtccacataa ctttgtggta gattccagtt cttgtgtcg tgcctgccct
 961 agttccaaga tggaagtaga agaaaatggg attaaaatgt gtaaaccttg cactgacatt
1021 tgcccaaaag cttgtgatgg cattggcaca ggatcattga tgtcagctca gactgtggat
1081 tccagtaaca ttgacaaatt cataaactgt accaagatca atgggaattt gatcttttcta
1141 gtcactggta ttcatgggga ccctacaat gcaattgaag ccatagaccc agagaaactg
1201 aacgtctttc ggacagtcag agagataaca ggtttcctga acatacagtc atggccacca
1261 aacatgactg acttcagtgt tttttctaac ctcaagcaa ctggtgacca ttggtgaag agtactctat
1321 agtgcctgt ccttgcttat cctcaagcaa cagggcatca ctctctaca acagcaacct gtgttattat
1381 ctgaaggaaa tcagcgcagg aaacatctat attactgaca acaatcaaac agagaatagt aatccgggac
1441 cataccatta actgacaac ctcttcagc acaatcaaac agagaatagt gcaaccatct gtgttccagt
1501 aacagaaaag ctgaaaattg tactgctgaa ggaatggtgt gcaaccatct gtcgcgctt cagtagagga
1561 gatgctgtt ggggacctgg gccagaccaa tgtctgtcgt gtcgcgcctt tcgggagtt tgagaatggc
1621 aggatctgca tagagtcttg taacctctat gatggtgaat ttcgggagatt aagatggcct cagtagagga
1681 tccatctgtg tggagtgtga cccccagtgt gagagagatgg aagatggcct cctcacatgc
```

FIG. 1A

```
   1 aattgtcagc acggatctg  agacttccaa aaaatgaagc cggcgacagg actttgggtc
  61 tgggtgagcc ttctcgtggc ggcggggacc gtccagccca gcgattctca gtcagtgtgt
 121 gcaggaacgg agaataaact gagctctctc tctgacctgg aacagcagta ccgagccttg
 181 cgcaagtact atgaaaactg tgaggttgtc atgggcaacc tggagataac cagcattgag
 241 cacaaccggg acctctcctt cctgcggtct gttcgagaag tcacaggcta cgtgttagtg
 301 gctcttaatc agtttcgtta cctgcctctg gagaatttac gcattattcg tgggacaaaa
 361 ctttatgagg atcgatatgc cttggcaata ttttttaaact acagaaaaga tggaaacttt
 421 ggacttcaag aacttgatt  aagaacttg  acagaaatcc taaatggtgg agtctatgta
 481 gaccagaaca aattcctttg ttatgcagac accattcatt ggcaagatat tgttcggaac
 541 ccatggcctt ccaacttgac tcttgtgtca acaaatggta gttcaggatg tggacgttgc
 601 cataagtcct gtactggccg ttgctgggga cccacagaaa atcattgcca gactttgaca
 661 aggacggtgt gtgcagaaca atgtgacggc agatgctacg gaccttacgt cagtgactgc
 721 tgccatcgag aatgtgctgg aggctgctca ggacctaagg acacagactg ctttgcctgc
 781 atgaatttca atgacagtgg agcatgtgtt actcagtgtc cccaaccttt tgtctacaat
 841 ccaaccacct ttcaactgga gcacaatttc aatgcaaagt acacatatgg agcattctgt
 901 gtcaagaaat gtccacataa ctttgtggta gattccagtt gattccagtt tgcctgccct
 961 agttccaaga tggaagtaga agaaaatggg attaaaatgt gtaaaccttg cactgacatt
1021 tgcccaaaag cttgtgatgg cattgcaca  ggatcattga tgtcagctca gactgtggat
1081 tccagtaaca ttgacaaatt cataaactgt accaagatca atgggaattt gatctttcta
1141 gtcactggta ttcatgggga cccttacaag gcaattgaag ccatagaccc agagaaactg
1201 aacgtctttc ggacagtcag agagataaca ggtttcctga acatacagtc atggccacca
1261 aacatgactg acttcagtgt tttttctaac ctgtgtgacca ttggtggaag agtactctat
1321 agtgcctgt  ccttgcttat cctcaagcaa cagggcatca cctctctaca gttccagtcc
1381 ctgaaggaaa tcagcgcagg aaacatctat attactgaca acagcaacct gtgttattat
1441 cataccatta actggacaac actcttcagc acaatcaaacc agagaatagt aatccggac
1501 aacagaaaag ctgaaaattg tactgctgaa ggaatggtgt gcaaccatct gtgttccagt
1561 gatggctgtt gggacctgg  gccagaccaa tgtctgtcgt gtcgccgctt cagtagagga
1621 aggatctgca tagagtcttg taacctctat gatggtgaat ttcgggagtt tgagaatggc
1681 tccatctgtg tggagtgtga cccccagtgt gagaagatgg aagatggcct cctcacatgc
```

FIG.1B

```
3541  ccttttgttt  ctcggagaaa  aaatgagagac  cttcaagcat  tggataatcc  cgaatatcac
3601  aatgcatcca  atgtcatcca  caaggccgag  gatgagtatg  tgaatgagcc  actgtacctc
3661  aacacctttg  ccaacaccct  gggaaaagct  gagtacctga  agaacaacat  actgtcaatg
3721  ccagagaagg  ccaagaaagc  gtttgacaac  cctgactact  ggaaccacag  cctgccacct  tttttataaa
3781  cggagcaccc  ttcagcaccc  agactacctg  caggagtaca  gcacaaaata  tgagttctcc
3841  cagaatgggc  ggatccggc   tattgtggca  gagaatcctg  aatacctctc  tgtggtgtaa
3901  ctgaagccag  gcactgtgct  gccgctcca   ccttacagac  accctgctc   acccccctct
3961  gctcagttgt  ggtttttag   gtggagagac  acacctgctc  caatttcccc  cccagtggaa
4021  ctttctctgg  tggtcttcct  tctacccaa   ggccagtagt  tttgacactt  gggaaagact
4081  gatacagaga  tgcaatgata  gttatgtgct  tacctaactt  gaacattaga  gttggtcagg
4141  gaaagagaaa  gataggagga  accacaatgt  ttcttcattt  ctctgcatgg  ctatcaaact
4201  agaatgaaac  agctagagaa  ggaccagaaa  atgtaaggca  atgctgccta  cttcttttt
4261  agctgtcact  tttttctttt  ttcttttct   ttctttgttt  ctttcttcct  ctgcaggaac
4321  tttttttttt  taaagcagat  ggttgaaaca  cccatgctat  ctgttcctat  gaacaaaaga
4381  tgatgtgtgc  atatttagca  tccctgaaa   tcataataaa  gttccatta   cttcccccag
4441  ataacattt   ctataacata  tgatagtgtc  tgaaattgag  aatccagttt  aaaatctcca
4501  cagttctgt   cctagcaagt  aagaatggcc  aactcaactt  tcataattta  tttgttttg
4561  ttaagttat   aactagtaat  tatgttttca  acacttttg   gtttttttca  aattgcaaag
4621  ctctgaccga  ttcctttata  tttgctcccc  tatttttggc  tttaatttct  atagtgaaat
4681  atgtttacat  caaagcttct  tcacagaatt  taagcaagaa  atattttaat  ttttttcatgc
4741  ggccactact  ttaagtatac  aatcttaa    ataagaaayg  gaggctaata  ctccataaat
4801  tatcaaatta  tcttcaccct  catccttac   atttttcaac  attttttt    gagacagttc
4861  gacactactt  gatagccgt   tggttgtctg  aagagtagaa  gggaaactaa  aatccattga
4921  tctgtggttc  aggaaaacta  ctgatactt   caggggtggc  ccaatgaggg  aatgtagttt
4981  actggaagaa  acacactgga  ttgggtatgt  ctacctggca  gatactcaga  tttgaatcaa
5041  gcacttaagc  tgtaattta   tttgttcttt  ttctgaactc  cattttggat  aaagagctaa
5101  gcaatatgga  agcaaccagc  aaattaacta  atttaagtac  attttaaaa   gtatccaggg
5161  gataaagact  gtggaaatgc  caaaccaagc  atatgtcacc  ccttgcaacg  aaggaaattt
5221  actatgatga  gaggccagca  cattatcttc  atatgtcacc  tttgctacgc  attccatgga
5281  gttcagttcg  tatacttcgt  aagaaggaat  gcgagtaagg  attggcttga  taaattggta
5341  atttctagta  tgagactatt  tatatgaagt  agaaggtaac  tctttgcaca  tcaaagtttg
5401  taataaaaag  aaaaaacaca  acattcaaag  cttaggata   ggtccttggg  tcaaagtttg
5461  taaataaatg  tgaaacatct  tctc
```

FIG. 1C

MKPATGLWVSLLVAAGTVQPSDSQSVCAGTENKLSSLSDLEQQYRALRKYYENCEVVMGNLE
ITSIEHNRDLSFLRSVREVTGYVLVALNQFRYLPLENLRIIRGTKLYEDRYALAIFLNYRKDGN
FGLQELGLKNLTEILNGGVVDQNKFLCYADTIHWQDIVRNPWPSNLTLVSTNGSSGCRCHKS
CTGRCWGPTENHCQTLTRTVCAEQCDGRCYGPYVSDCCHRECAGGCSGPKDTDCFACMNFNDSG
ACVTQCPQTFVYNPTTFQLEHNFNAKYTYGAFCVKKCPHNFVVDSSSCVRACPSSKMEVEENGI
KMCKPCTDICPKACDGIGTGSLMSAQTVDSSNIDKFINCTKINGNLIFLVTGIHGDPYNAIEAI
DPEKLNVFRTVREITGFLNIQSWPPNMTDFSVFSNLVTIGGRVLYSGLSLLILKQQGITSLQFQ
SLKEISAGNIYITDNSNLCYYHTINWTTLFSTINQRIVIRDNRKAENCTAEGMVCNHLCSSDGC
WGPGPDQCLSCRRFSRGRICIESCNLYDGEFREFENGSICVECDPQCEKMEDGLLTCHGPGPDN
CTKCSHFKDGPNCVEKCPDGLQGANSEIFKYADPDRECHPCHPNCTQGCNGPTSHDCIYPWTG
HSTLFPQHARTPLIAAGVIGGLFILVIGLTFAVYVRRKSIKKKRALRFELETELVEPLTPSGTA
PNQAQLRILKETELKRVKVLGSGAFGTVYKGIWVPEGETVKIPVAIKILNETTGPKANVEFMDE
ALIMASMDHPHLVRLLGVCLSPTIQLVTQLMPHGCLLFYVHEHKDNIGSQLLLNWCVQIAKGMM
YLEERRLVHRDLAARNVLVKSPNHVKITDFGLARLLEGDEKEYNADGGKMPIKWMALECIHYRK
FTHQSDVWSYGVTIWELMTFGGKPYDGIPTREIPDLLEKGERLPQPPICTIDVYMVKCWMID
ADSRPKFKELAAEFSRMARDPQRYLVIQGDDRMKLPSPNDSKFFQNLLDEEDLEDLEDMDAEEYLV
PQAFNIPPPIYTSRARIDSNRSEIGHSPPAYTPMSGNQFVYRDGGFAAEQGVSVPYRAPTSTI
PEAPVAQGATAEIFDDSCCNGTLRKPVAPHVQEDSSTQRYSADPTVFAPERSPRGELDEEGYMT
PMRDKPKQEYLNPVEENPFVSRRKNGDIQALDNPEYHNASNGPPKAEDEYVNEPLYLNTFANTL
GKAEYLKNNILSMPEKAKKAFDNPDYWNHSLPPRSTLQHPDYLQEYSTKYFYKQNGRIRPIVAE
NPEYLSEFSLKPGTVLPPPPYRHRNTVV

FIG. 2

```
ccaatcgatttcgcggcaaagaccttccggtcctggaccagctgctcgagcagtcagtgtgtgcaggaac
ggagaataaactgagctctctctgacctggaacagcagtaccgagccttgcgcaagtactatgaaaac
tgtgaggttgtcatgggcaacctggagataaccagcattgagcacaaccggacctctccttcctgcgt
ctgttcgagaagtcacaggctacgtgttagtgctcttaatcagttcgttacctgcctctggagaattt
acgcattattcgtgggacaaaactttatgaggatcgatatgcctggcaatatttttaaactacagaaaa
gatggaaactttggacttcaagaacttggattaaagaacttgacagaaatcctaaatggtggagtctatg
tagaccagaacaaattcctttgttatgcagacaccattcattgcaagatattgttcgaaccatggcc
ttccaacttgactcttgtgtcaacaaatggtagttcaggatgtgacgttgccataagtcctgtactggc
cgttgctgggaccacttacgctgactgctgccatcgagatttgacaaggacggtgtgtgcagaacaatgtgacg
gcagatgctacggaccttgctgctgcatgaatttcaatgacagtggagcatgtgttactcagtgtcccaaacc
ggacacagactgctttgcctgcatgaatttcaactggagcacaatttcaatgcaaagtacacatatgagcattct
tttgtctacaatccaaccacccttcaactctttgtggtagattcccagttccaagttctgtgctgcctgccctagttccaa
gtgtcaagaaaatgtccacataactttgtggtagattctaaaatgtgtaaacctggatccaagatgttgatcatgtgtga
ggcattggcacacaggatcattgatgtcagctcagactgtgagatccagtaacattgacaaattcataaact
gtaccaagatcaatggaatttgatctttctagtcactgtattcatggaccctacaatgcaattga
agccatagacccagagaaaactgactgacttcagtgtttttctaacctggtgaccattggtggaagagtactct
tcatgccaccaaacatgactgacttcagtgtttttctaacctggtgaccattggtgaagagtactct
atagtggcctgtccttatcctcaagcaacaggcatcacctctcacagttccagtccctgaagga
aatcagcgcaggaaaacatctatattactgacaacagcaaacctgtgttattatcataccattaactggaca
acactcttcagcacacaatcaaccagagaataagtaatccggacaacagaaagctgaaaattgtactgctg
aaggaatggttgcaaccatctgtgttccagtgatggctgttgggaacctggggacctggccaatgtctgtc
gtgtcgccgcttcagtgagggaag
```

FIG. 3A

```
gatctgcatagagtcttgtaacctctctatgatgtgaatttcgggagtttgagaatggctccatctgtgtg
gagtgaccccagtgtgagaagatggaagatggcctccatcacatgccatggaccggtcctgacaact
gtacaaagtgctctcatttttaaagatggcccaaactgtgtggaaaaatgtccagatggcttacagggggc
aaacagtttcattttcaagtatgctgatcgatctgatcgatactgcatccacctgccatccaaactgcacccaa
gggtgtaacggtcccactagtcattactgactgcatgacgggcacgcgtgacaaaactcaca
catgcccaccgtgcccagcacctgaactcctgggggaccgtcagtcttcctcttccccccaaaacccaa
ggacaccctcatgatctcccgacccctgagttcacatgcgtggtggacgtgagccacgaagacccct
gaggtcaagttcaactgtacgggtgatggacggcgtggaggtgcataatgccaagacaaagccgcgggaggagc
agtacaacagcacgtaccggtgtgtcagcgtcctcaccgtcctgcaccaggactggctgaatggcaagga
gtacaagtgcaaggtctccaacaaagccctcccagcccccatcgagaaaaccatctccaaagccaaaggg
cagccccgagaaccacaggtgtacaccctgcccccatcccgggaagagagatgaccaagaaccaggtcagcc
tgacctgcctggtcaaaggcttctatcccagcgacatcgccgtggagtgggagagcaatgggcagccgga
gaacaactggcccaccccctggcttacaagaccacgcctcccgtgctggactccgacggctccttcttc
ctctacagcaagctcaccgtggacaagagcaggtggcaggggaacgtcttctcatgctctccgtgatgc
atgaggctctgcacaaccactacacgcagaagagcctctccctgtctccgggtaaat
```

FIG. 3B

```
QSVCAGTENKLSSLSDLEQQYRALRKYYENCEVVMGNLEITSIEHNRDLSEFLRSVREVTGYVLV
ALNQFRYLPLENLRIIRGTKLYEDRYALAIFLNYRKDGNFGLQELGLKNLTEILNGGVYVDQNK
FLCYADTIHWQDIVRNPWPSNLTLVSTNGSSGCGRCHKSCTGRCWGPTENHCQTLRTVCAEQC
DGRCYGPYVSDCCHRECAGGCSGPKDTDCFACMNFNDSGACVTQCPQTFVYNPTTFQLEHNFNA
KYTYGAFCVKKCPHNFVVDSSSCVRACPSSKMEVEENGIKMCKPCTDICPKACDGIGTGSLMSA
QTVDSSNIDKFINCTKINGNLIEFLVTGIHGDPYNAIEAIDPEKLNVFRTVREITGFLNIQSWPP
NMTDFSVFSNLVTIGGRVLYSGLSLLILKQQGITSLQFQSLKEISAGNIYITDNSNLCYYHTIN
WTTLFSTINQRIVIRDNRKAENCTAEGMVCNHLCSSDGCWGPGPDQCLSCRRFSRGRICIESCN
LYDGEFREFENGSICVECDPQCEKMEDGLLTCHGPGPDNCTKCSHFKDGPNCVEKCPDGLQGAN
SFIFKYADPDRECHPCHPNCTQGCNGPTSHDCIYPWTG
```

FIG. 4 ent application Ser. No. 09/940,101 filed Aug. 27, 2001, now abandoned and which claims benefit under 35 U.S.C. § 119(e) of U.S. Provisional Patent Application Ser. No. 60/265,516 filed Jan. 31, 2001 and of U.S. Provisional Patent Application Ser. No. 60/229,679 filed Sep. 1, 2000.

ANTIBODIES TO HUMAN ERBB4

CROSS-REFERENCE TO RELATED APPLICATIONS

This application is a 371 of PCT/US01/26984 filed Aug. 29, 2001 which is a continuation of U.S. patent application Ser. No. 09/940,101 filed Aug. 27, 2001, now abandoned and which claims benefit under 35 U.S.C. § 119(e) of U.S. Provisional Patent Application Ser. No. 60/265,516 filed Jan. 31, 2001 and of U.S. Provisional Patent Application Ser. No. 60/229,679 filed Sep. 1, 2000.

BACKGROUND OF THE INVENTION

1. Field of the Invention

The present invention concerns methods and means for controlling excessive proliferation and/or migration of smooth muscle cells, and in particular for treating stenosis, by using antagonists of a native ErbB4 receptor. The invention further concerns a method for the identification of ErbB4 agonists and antagonists capable of inhibiting or enhancing the proliferation or migration of smooth muscle cells.

2. Description of the Related Art

1. ErbB Receptor Tyrosine Kinases

Transduction of signals that regulate cell growth and differentiation is regulated in part by phosphorylation of various cellular proteins. Protein tyrosine kinases are enzymes that catalyze this process. Receptor protein tyrosine kinases are believed to direct cellular growth via ligand-stimulated tyrosine phosphorylation of intracellular substrates.

HER4/Erb4 is a receptor protein tyrosine kinase belonging to the ErbB family. Increased ErbB4 expression closely correlates with certain carcinomas of epithelial origin, including breast adenocarcinomas (Plowman et al., Proc. Natl. Acad. Sci. USA 90:1746-1750 [1993]; Plowman et al., Nature 366:473-475 [1993]). Diagnostic methods for detection of human neoplastic conditions (especially breast cancers) which evaluate ErbB4 expression are described in EP Pat Appln No. 599,274.

Other members of the ErbB family of receptor tyrosine kinases include: epidermal growth factor receptor (EGFR), ErbB2 (HER2/neu), and ErbB3 (HER3). The erbB1 gene encodes the 170 kDa epidermal growth factor receptor (EGFR) that has been causally implicated in human malignancy. In particular, increased expression of this gene has been observed in more aggressive carcinomas of the breast, bladder, lung and stomach (Modjitahedi, H. and Dean, C. (1994) Int. J. Oncol. 4:277-296). HER4 acts, in the absence of HER2, as a mediator of antiproliferative and differentiative response in human breast cancer cell lines. (Sartor et al., Mol. Cell Biol. 21:4265-75 (2001)).

The neu gene (also called erbB2 and HER2) encodes a 185 kDa receptor protein tyrosine kinase that was originally identified as the product of the transforming gene from neuroblastomas of chemically treated rats. Amplification and/or overexpression of the human HER2 gene correlates with a poor prognosis in breast and ovarian cancers (Slamon, D. J. et al., Science 235:177-182 (1987); Slamon et al., Science 244:707-712 (1989); and U.S. Pat. No. 4,968,603). Overexpression of HER2 (frequently but not uniformly due to gene amplification) has also been observed in other carcinomas including carcinomas of the stomach, endometrium, salivary gland, lung, kidney, colon, thyroid, pancreas and bladder.

A further related gene, called erbB3 or HER3, has been described. See U.S. Pat. No. 5,183,884; Kraus et al., Proc. Natl. Acad. Sci. USA 86:9193-9197 (1989); EP Pat Appln No 444,961 A1; and Kraus et al., Proc. Natl. Acad. Sci. USA 90:2900-2904 (1993). Kraus et al. (1989) discovered that markedly elevated levels of erbB3 mRNA were present in certain human mammary tumor cell lines indicating that erbB3, like erbB1 and erbB2, may play a role in human malignancies. They also showed that EGF-dependent activation of the ErbB3 catalytic domain of a chimeric EGFR/ErbB3 receptor resulted in a proliferative response in transfected NIH-3T3 cells. Furthermore, these researchers demonstrated that some human mammary tumor cell lines display a significant elevation of steady-state ErbB3 tyrosine phosphorylation further indicating that this receptor may play a role in human malignancies. The role of erbB3 in cancer has been explored by others. It has been found to be overexpressed in breast (Lemoine et al., Br. J. Cancer 66:1116-1121 (1992)), gastrointestinal (Poller et al, J. Pathol. 168:275-280 (1992), Rajkumer et al., J. Pathol. 170:271-278 (1993), and Sanidas et al., Int. J. Cancer 54:935-940 (1993)), and pancreatic cancers (Lemoine et al., J. Pathol. 168:269-273 (1992), and Friess et al., Clinical Cancer Research 1:1413-1420 (1995)). ErbB3 is unique among the ErbB receptor family in that it possesses little or no intrinsic tyrosine kinase activity (Guy at al., Proc. Natl. Acad. Sci. USA 91:8132-8136 (1994) and Kim at al. J. Biol. Chem. 269:24747-55 (1994)).

The ErbB receptors are generally found in various combinations in cells and heterodimerization is thought to increase the diversity of cellular responses to a variety of ErbB ligands (Earp et al Breast Cancer Research and Treatment 35: 115-132 (1995)). EGFR is bound by six different ligands; epidermal growth factor (EGF), transforming growth factor alpha (TGF-), amphiregulin, heparin binding epidermal growth factor (HB-EGF), β-cellulin and epiregulin (Groenen at al. Growth Factors 11:235-257 (1994)). A family of heregulin proteins resulting from alternative splicing of a single gene are ligands for ErbB3 and ErbB4. The heregulin family includes α, β and γ heregulins (Holmes at al, Science, 256:1205-1210 (1992); U.S. Pat. No. 5,641,869; and Schaefer et al. Oncogene 15:1385-1394 (1997)); neu differentiation factors (NDFs), glial growth factors (GGFs); acetylcholine receptor inducing activity (ARIA); and sensory and motor neuron derived factor (SMOF). For a review, see Groenen et al. Growth Factors 11:235-257 (1994); Lemke, G. Molec. & Cell. Neurosci. 7:247-262 (1996) and Lee at al. Pharm. Rev. 47:51-85 (1995). Recently three additional ErbB ligands were identified; neuregulin-2 (NRG-2) which is reported to bind either ErbB3 or ErbB4 (Chang et al Nature 387 509-512 (1997); and Carraway et al Nature 387:512-516 (1997)); neuregulin-3 which binds ErbB4 (Zhang at al. PNAS (USA) 94(18): 9562-7 (1997)); and neuregulin-4 which binds ErbB4 (Harari at al Oncogene 18:2681-89 (1999)). HB-EGF, β-cellulin and epiregulin also bind to ErbB4.

While EGF and TGF do not bind ErbB2, EGF stimulates EGFR and ErbB2 to form a heterodimer, which activates EGFR and results in transphosphorylation of ErbB2 in the heterodimer. Dimerization and/or transphosphorylation appear to activate the ErbB2 tyrosine kinase. See Earp et al., supra. Likewise, when ErbB3 is co-expressed with ErbB2, an active signaling complex is formed and antibodies directed against ErbB2 are capable of disrupting this complex (Sliwkowski et al, J. Biol. Chem., 269(20):14661-14665 (1994)). Additionally, the affinity of ErbB3 for heregulin (HRG) is increased to a higher affinity state when co-expressed with ErbB2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.*, 56:1457-1465 (1996) with respect to the ErbB2-ErbB3 protein complex. ErbB4, like ErbB3, forms an active signaling complex with ErbB2 (Carraway and Cantley, *Cell* 78:5-8 (1994)).

Because of the physiological importance, members of the ErbB family of receptor tyrosine kinases have often been targeted for therapeutic development. For example, Hudziak et al., *Mol. Call. Biol.* 9(3):1165-1172 (1989) describe the generation of a panel of anti-ErbB2 antibodies one of which, called 4D5, inhibited cellular proliferation by 56%. A recombinant humanized version of the murine anti-ErbB2 antibody 4D5 (huMAb4D5-8, rhuMAb HER2 or HERCEPTIN®; U.S. Pat. No. 5,821,337) is clinically active in patients with ErbB2-overexpressing metastatic breast cancers that have received extensive prior anti-cancer therapy (Baselga et al., *J. Clin. Oncol.* 14:737-744 (1996)). HERCEPTIN® received marketing approval from the Food and Drug Administration Sep. 25, 1998 for the treatment of patients with metastatic breast cancer whose tumors overexpress the ErbB21HER2 protein. Since HER2 is also overexpressed in other cancers, in addition to breast cancer, HERCEPTIN® holds a great potential in the treatment of such other cancers as well.

2. Smooth Muscle Cell Proliferation

Smooth muscle cells are very important structural and functional components of many hollow passages in the body, including blood vessels, gastrointestinal tract, airway passage (trachea and bronchi in lungs), urinary tract system (bladder and ureters) etc. They are responsible for elasticity that is so crucially required for normal functioning of these organs. They respond to a variety of physiological stimuli by constriction or dilation as needed, for example, for regulating the flow of fluids carried by them. They respond not only to chemical stimuli, such as growth factors and cytokines, but also to physical stimuli, such as pressure and stretch. Excessive proliferation of smooth muscle cells results in thickening of the wall and narrowing the lumen of the organs known as "stenosis" in a variety of disorders.

A number of growth factors and cytokines are implicated in the proliferation of smooth muscle cells. One category of such important molecules are EGF related ligands. For example, smooth muscle cells from a variety of such organs have been demonstrated to possess EGF receptors, and some of them even synthesize and secrete EGF ligands such as HB-EGF, thus setting up autocrine loop. Various EGF ligands act as potent mitogens and stimulate proliferation of smooth muscle cells often resulting in thickening of the wall and ultimately stenosis. For example, excessive proliferation of vascular smooth muscle cells (VSMC) is involved in pathology of vascular stenosis, restenosis resulting from angioplasy or surgery or stent implants, atherosclerosis, transplant atherosclerosis and hypertension (reviewed in Casterella and Teirstein, *Cardiol. Rev.* 7: 219-231 [1999]; Andres, *Int. J. Mol. Med.* 2: 81-89 [1998]; and Rosanio at al, *Thromb. Haemost.* 82 [suppl 1]: 164-170 [1999]). The thickening of blood vessels increases resistance to blood flow and ultimately leads to hypertension. Moreover, decreased blood supply to the tissue may also cause necrosis and induce inflammatory response leading to severe damage. For example, myocardial infarction occurs as a result of lack of oxygen and local death of heart muscle tissues.

Infantile hypertrophic pyloric stenosis (IHPS), which causes functional obstruction of the pyloric canal also involves hypertrophy and hyperplasia of the pyloric smooth muscle cells (Due and Puri, *Pediatr. Res.* 45: 853-857 [1999]). Furthermore, EGF, EGF receptor and HB-EGF are implicated in pathogenesis of pyloric stenosis (Shima et al., *Pediatr. Res.* 47: 201-207 [2000]).

Similarly, the urinary bladder wall thickening that occurs in response to obstructive syndromes affecting the lower urinary tract involves proliferation of urinary bladder smooth muscle cells. A membrane-bound precursor form of HB-EGF is expressed in urinary bladder smooth muscle cells and HB-EGF is a potent mitogen for bladder SMC proliferation (Freeman et al., *J. Clin. Invest.* 99: 1028-1036 [1997]; Kaefer et al., *J. Urol.* 163: 580-584 [2000]; Borer et al., *Lab Invest.* 79: 1335-1345 [1999]).

The obstructive airway diseases are yet another group of diseases with underlying pathology involving smooth muscle cell proliferation. One example of this group is asthma which manifests in airway inflammation and bronchoconstriction. EGF is implicated in the pathological proliferation of airway SMCs in obstructive airway diseases (Cerutis et al., *Am. J. Physiol.* 273: L10-15 [1997]; Cohen et al, *Am. J. Respir. Cell. Mol. Biol.* 16: 85-90 [1997]).

The instant invention discloses the use of ErbB4 receptor antagonists for controlling excessive migration and/or proliferation or smooth muscle cells and, in particular, for the treatment of stenosis.

SUMMARY OF THE INVENTION

In one aspect, the invention concerns a method for controlling excessive proliferation or migration of smooth muscle cells by treating the smooth muscle cells with an effective amount of an antagonist of a native ErbB4 receptor. The control is prevention or inhibition, including total inhibition, of excessive proliferation or migration of smooth muscle cells. In one embodiment the smooth muscle cells are urinary bladder smooth muscle cells, and in another embodiment they are the smooth muscle cells of an airway passage.

The excessive proliferation or migration of smooth muscle cells such as vascular smooth muscle cells may result in stenosis including vascular stenosis and restenosis. In one embodiment the smooth muscle cells are human.

The stenosis may be further characterized by excessive proliferation or migration of endothelial cells.

In one embodiment the ErbB4 receptor antagonist is an immunoadhesin. In another embodiment the ErbB4 receptor antagonist is an antibody, such as a neutralizing antibody against a native ErbB4 receptor.

In another aspect, the invention concerns a method for treating stenosis in a mammalian patient, including a human, comprising administering to the patient an effective amount of an antagonist of a native mammalian ErbB4 receptor. The treatment includes prevention of stenosis. The stenosis may be vascular stenosis including restenosis. The antagonist may be administered as an injection or infusion. The treatment may also be used to reduce hypertension associated with the stenosis. The stenosis may be vascular stenosis including restenosis, pyloric stenosis, thickening of the urinary bladder wall or part of an obstructive airway disease.

In one embodiment the antagonist is an immunoadhesin, which may comprise the extracellular region of a native human ErbB4 receptor. In another embodiment the antagonist is an antibody, such as a neutralizing antibody against a native human ErbB4 receptor.

In a further aspect, the invention concerns a method for treating stenosis in a mammalian patient, such as a human, comprising introducing into a cell of the patient a nucleic acid encoding an antagonist of an ErbB4 receptor. The nucleic acid may be introduced in vivo or ex vivo, and with the aid of a vector such as retroviral vector or a lipid based delivery system. The method of the present invention is particularly useful for the treatment (including prevention) of vascular stenosis and restenosis.

The antagonist may be an immunoadhesin. The antagonist may also be an antibody, such as a neutralizing antibody against a native human ErbB4 receptor.

In another aspect, the invention concern a method for treating hypertension associated with vascular stenosis in a mammalian patient, comprising administering to the patient an effective amount of an antagonist of a native ErbB4 receptor. The antagonist may be a small molecule.

In a still further aspect, the invention concerns a pharmaceutical composition for the treatment of stenosis in a mammalian patient comprising an effective amount of an antagonist of a native mammalian ErbB4 receptor, in admixture with a pharmaceutically acceptable carrier.

In all aspects, preferred ErbB4 antagonists include immunoadhesins, preferably comprising a native human ErbB4 receptor extracellular domain sequence fused to an immunoglobulin constant region sequence. The immunoglobulin sequence preferably is that of a heavy chain constant region of an IgG1, IgG2 or IgG3 immunoglobulin and may additionally comprise an immunoglobulin light chain sequence covalently attached to the fusion molecule comprising the immunoglobulin heavy chain constant region.

Another preferred class of ErbB4 antagonists comprises neutralizing antibodies specifically binding a native ErbB4 receptor. The antibodies preferably are human or humanized. In one embodiment the antibodies bind essentially the same epitope as an antibody produced by a hybridoma selected from the group consisting of HER4.01H1.1A1 (ATCC Accession Number PTA-2828), HER4.1C6.A11 (ATCC Accession Number PTA-2829), HER4.3B9.2C9 (ATCC Accession Number PTA-2826), HER4.1A6.5B3 (ATCC Accession Number PTA-2827) and HER4.8B1.2H2 (ATCC Accession Number PTA-2825). The antibodies may also have complementarity determining region (CDR) residues from an antibody produced by a hybridoma selected from the group consisting of HER4.10H1.1A1 (ATCC Accession Number PTA-2828), HER4.1C6.A11 (ATCC Accession Number PTA-2829), HER4.3B9.2C9 (ATCC Accession Number PTA-2826), HER4.1A6.5B3 (ATCC Accession Number PTA-2827) and HER4.8B1.2H2 (ATCC Accession Number PTA-2825).

The smooth muscle cells may, for example, be pyloric or urinary bladder smooth muscle cells, or smooth muscle cells of an airway passage. Preferably, the smooth muscle cells are vascular smooth muscle cells.

In a still further aspect, the invention concerns a method for identifying a molecule that inhibits or enhances the proliferation or migration of smooth muscle cells, comprising the steps of: (a) contacting a polypeptide comprising an amino acid sequence having at least 85% sequence identity with the amino acid sequence of the extracellular domain of a native ErbB4 receptor and retaining the ability to control excessive proliferation or migration of smooth muscle cells, with a candidate molecule; and (b) determining whether the candidate molecule inhibits or enhances the ability of the polypeptide to control excessive proliferation or migration of smooth muscle cells. The polypeptide may comprise the extracellular domain of a native ErbB4 receptor. The polypeptide is an immunoadhesin in one embodiment. In a particular embodiment, the molecule enhances the ability of the polypeptide to control excessive proliferation or migration of smooth muscle cells, and is an antibody or a small molecule.

In a yet further aspect the invention concerns an antibody that binds essentially the same epitope of ErbB4 as an antibody produced by a hybridoma selected from the group consisting of HER4.10H1.1A1 (ATCC Accession Number PTA-2828), HER4.1C6.A11 (ATCC Accession Number PTA-2829), HER4.3B9.2C9 (ATCC Accession Number PTA-2826), HER4.1A6.5B3 (ATCC Accession Number PTA-2827) and HER4.8B1.2H2 (ATCC Accession Number PTA 2825). In addition to the methods set forth above and throughout the disclosure, these antibodies are believed to be useful in the treatment of various cancers, including breast cancer.

In a still further aspect the invention concerns an antibody that has complementarity determining region (CDR) residues from an antibody produced by a hybridoma selected from the group consisting of HER4.10H1.1A1 (ATCC Accession Number PTA-2828), HER4.1C6.A11 (ATCC Accession Number PTA-2829), HER4.3B9.2C9 (ATCC Accession Number PTA-2826), HER4.1A5.5B3 (ATCC Accession Number PTA-2827) and HER4.8B1.2H2 (ATCC Accession Number PTA-2825).

In a further aspect the invention concerns an antibody selected from the group consisting of an antibody produced by a hybridoma selected from the group consisting of HER4.10H1.1A1 (ATCC Accession Number PTA-2828), HER4.1C6.A11 (ATCC Accession Number PTA-2829), HER4.3B9.2C9 (ATCC Accession Number PTA-2826), HER4.1A6.5B3 (ATCC Accession Number PTA-2827) and HER4.8B1.2H2 (ATCC Accession Number PTA-2825)

The invention also concerns an antibody that binds essentially the same epitope of ErbB4 bound by an antibody selected from the group consisting of anti-ErbB4 monoclonal antibodies 4-1440, 4-1460, 4-1473, 4-1492 and 4-1464.

Further, the invention concerns an antibody that has complementarity determining region (CDR) residues from an antibody selected from the group consisting of anti-ErbB4 monoclonal antibodies 4-1440, 4-1460, 4-1473, 4-1492 and 4-1464.

The invention also concerns an antibody that binds ErbB4 with high affinity. This antibody preferably binds to ErbB4 with a Kd of less than 100 nM, more preferably with a Kd of less than 50 nM, even more preferably with a Kd of less than 25 nM and most preferably with a Kd less than 10 nM. In one embodiment this antibody is a human antibody and in another embodiment it is a humanized antibody. In yet another embodiment the antibody is an antibody fragment.

The invention further concerns an antibody which is capable of binding to both ErbB4 and ErbB3. In one embodiment the antibody is capable of binding ErbB4 with high affinity and in another embodiment the antibody binds both ErbB4 and ErbB3 with high affinity.

In another aspect the invention concerns an antibody which binds to ErbB4 and reduces heregulin binding thereto. This antibody may bind ErbB4 with high affinity.

Finally, the invention concerns an antibody which binds to ErbB4 and reduces heregulin-induced tyrosine phosphorylation thereof. This antibody may also bind ErbB4 with high affinity.

BRIEF DESCRIPTION OF THE DRAWINGS

FIGS. 1A, 1B and 1C show the nucleotide sequence of human ErbB4 (SEQ ID NO:1).

FIG. 2 shows the deduced amino acid sequence of human ErbB4 (SEQ ID NO: 2).

FIGS. 3A and 3B show the nucleotide sequence of an ErbB4-IgG immunoadhesin (SEQ ID NO:3).

FIG. 4 shows the amino acid sequence of the ErbB4 extracellular domain (ECD), which comprises amino acids 26 through 640 (SEQ ID NO: 4) of the ErbB4 amino acid sequence presented in FIG. 2 (SEQ ID NO: 2).

DETAILED DESCRIPTION OF THE PREFERRED EMBODIMENT

A. Definitions

Figure 5:
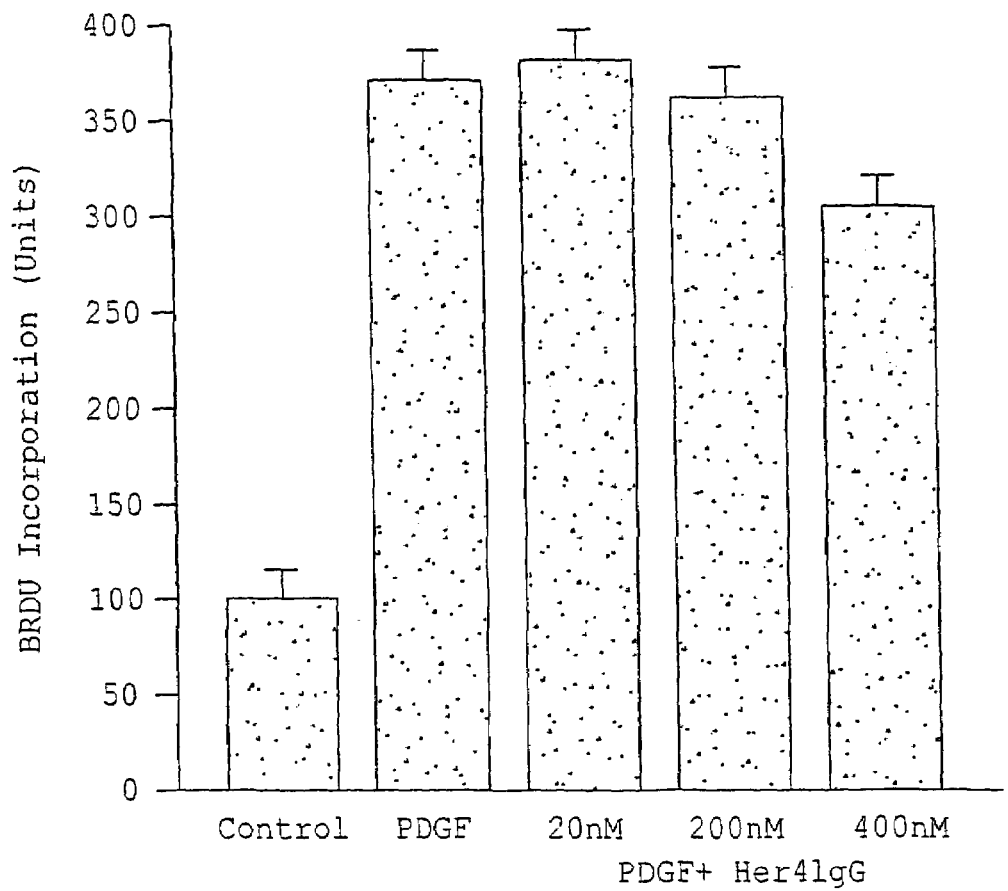
FIG. 5 shows the effect of ErbB4-IgG immunoadhesin on PDGF-stimulated proliferation of human aortic smooth muscle cells.

Unless defined otherwise, technical and scientific terms used herein have the same meaning as commonly understood by one of ordinary skill in the art to which this invention belongs. See, e.g. Singleton et al., *Dictionary of Microbiology and Molecular Biology 2nd ed.*, J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

Unless indicated otherwise, the term "ErbB" when used herein refers to any one or more of the mammalian ErbB receptors (i.e. ErbB1 or epidermal growth factor (EGF) receptor; ErbB2 or HER2 receptor; ErbB3 or HER3 receptor; ErbB4 or HER4 receptor; and any other member(s) of this class I tyrosine kinase family to be identified in the future) and "erbB" refers to the mammalian erbB genes encoding these receptors.

The terms "ErbB4" and "HER4" are used interchangeably and refer to a native sequence ErbB4 receptor polypeptide as disclosed, for example, in European Patent Application No. (EP) 599,274; Plowman at al., *Proc. Natl. Acad. Sci. USA*, 90:1746-1750 (1993); and Plowman et al., *Nature*, 366:473-475 (1993), and functional derivatives, including amino acid sequence variants thereof.

A "native" or "native sequence" ErbB4 or HER4 receptor has the amino acid sequence of a naturally occurring ErbB4 receptor in any mammalian (including humans) species, irrespective of its mode of preparation. Accordingly, a native or native sequence ErbB4 receptor may be isolated from nature, produced by techniques of recombinant DNA technology, chemically synthesized, or produced by any combinations of these or similar methods. Native ErbB4 receptors specifically include polypeptides having the amino acid sequence of naturally occurring allelic variants, isoforms or spliced variants of ErbB4, known in the art or hereinafter discovered. Native sequence ErbB4 receptors are disclosed, for example, in EP 599,274, supra, and in the two Plowman et al. papers, supra. Elenius et al., *J. Biol. Chem.* 272:26761-26768 (1997) report the identification of two alternatively spliced isoforms of ErbB4 both in mouse and human tissues, that differ by the insertion of either 23 (HER4 JM-a) or 13 (HER4 JM-b) alternative amino acids in the extracellular juxtamembrane (JM) region. Elenius et al., *Oncogene* 18:2607-2615 (1999) report the identification and characterization of another naturally occurring isoform of ErbB4 (designated as ErbB4 CYT-2), with a deletion of the cytoplasmic domain sequence required for the activation of the PI3-K intracellular signal transduction pathway. HER4 isoforms are also disclosed in WO 99/19488. A nucleotide sequence encoding ErbB4 is presented in FIG. 1 (SEQ ID NO: 1) and the corresponding deduced amino acid sequence is depicted in FIG. 2 (SEQ ID NO: 2).

The term "ErbB4 extracellular domain" or "ErbB4 ECD" refers to a soluble fragment of ErbB4 comprising the amino acids located between the signal sequence and the first predicted transmembrane region. In one embodiment, the "ErbB4 ECD" is a polypeptide comprising amino acids 26-640 (SEQ ID NO: 4) of the human ErbB4 sequence presented in FIG. 2 (SEQ ID NO: 2).

The term "mammal" is used herein to refer to any animal classified as a mammal, including, without limitation, humans, domestic and farm animals, and zoo, sports, or pet animals, such as sheep, dogs, horses, cats, cows, etc. Preferably, the mammal herein is human.

"Functional derivatives" include amino acid sequence variants, and covalent derivatives of the native polypeptides as long as they retain a qualitative biological activity of the corresponding native polypeptide. Amino acid sequence variants generally differ from a native sequence in the substitution, deletion and/or insertion of one or more amino acids anywhere within a native amino acid sequence. Deletional variants include fragments of the native polypeptides, and variants having N- and/or C-terminal truncations. Ordinarily, amino acid sequence variants will possess at least about 70% homology, preferably at least about 80%, more preferably at least about 90% homology with a native polypeptide.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

An ErbB "antagonist" is a molecule, which prevents or interferes with an ErbB effector function, e.g. a molecule, which prevents or interferes with binding and/or activation of a native sequence ErbB receptor by a ligand, and/or downstream pathways used by the native sequence ErbB receptor. Such molecules can be screened, for example, based upon their ability to competitively inhibit ErbB receptor activation by ligand in the tyrosine phosphorylation assay. Similarly, an antagonist of a native sequence ErbB4 (HER4) receptor is a molecule which prevents or interferes with an ErbB4 effector function, e.g. a molecule which prevents or interferes with binding and/or activation of a native sequence ErbB4 receptor by a ligand, and/or downstream pathways used by the ErbB4 receptor. Such molecules can be screened, for example, based upon their ability to competitively inhibit ErbB4 receptor activation by ligand in the tyrosine phosphorylation assay. Examples of ErbB4 antagonists include, without limitation, soluble ErbB4 receptors (such as extracellular domains (ECD) of native sequence and variant ErbB4 receptors), neutralizing antibodies against native sequence ErbB4 receptors, neutralizing antibodies to ligands of native sequence ErbB4 receptors (e.g. anti-HB-EGF antibodies), ErbB4-Ig immunoadhesins (including chimeric heteroadhesins) and small molecules.

By "ErbB4 ligand" is meant a polypeptide which binds to and/or activates an ErbB4 receptor. ErbB4 ligands include betacellulin, epiregulin, HB-EGF, NRG-2, NRG-3 and heregulins.

In the methods of the present invention, the term "control" and grammatical variants thereof, are used to refer to the prevention, partial or complete inhibition, reduction, delay or slowing down of an unwanted event, e.g. physiological condition, such as the excessive proliferation and/or migration of smooth muscle cells and/or other cell types, e.g. endothelial cells.

The term "excessive proliferation and/or migration" means proliferation and/or migration beyond normal levels that results or is likely to result, if untreated, in the development of an unwanted physiological condition or disease, such as, for example, stenosis, including vascular stenosis, restenosis, and pyloric stenosis; urinary bladder wall thickening, and obstructive airway disease.

"Treatment" refers to both therapeutic treatment and prophylactic or preventative measures. Those in need of treatment include those already with the disorder as well as those prone to have the disorder or those in which the disorder is to be prevented. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "isolated" molecule is defined broadly as a molecule that is identified and separated from at least one contaminant molecule with which it is ordinarily associated in the natural source of the molecule. Preferably, the isolated molecule is free of association with all components with which it is naturally associated.

The term immunoadhesin" as used herein refers to antibody-like molecules that combine the binding domain of a protein such as an extracellular domain (the adhesin portion) of a cell-surface receptor with the effector functions of an immunoglobulin constant domain. The term "immunoadhesin" specifically includes native or variant ErbB4 receptor sequences. The nucleic acid sequence of an ErbB4-IgG immunoadhesin is presented in FIG. 3 (SEQ ID NO: 3). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. The term "isolated immunoadhesin" refers to an immunoadhesin that has been purified from a source or has been prepared by recombinant or synthetic methods and is sufficiently free of other peptides or proteins.

Immunoadhesins reported in the literature include fusions of the T cell receptor (Gascoigne at al., Proc. Natl. Acad. Sci. USA 84:2936-2940 (1987)1; CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin or homing receptor (Watson et al., J. Cell. Biol. 110:2221:2229 (1990); and Watson at al., Nature 349:164-167 (1991)); CD44 (Aruffo at al., Cell 61:1303-1313 (1990)); CD28 and B7 (Linsley et al., J. Exp. Med. 173: 721-730 (1991)); CTLA-4 (Lisley at al., J. Exp. Med. 174:561-569 (1991)); CD22 (Stamenkovic at al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel at al., J. Exp. Med. 174:1483-1489 (1991)); NP receptors (Bennett et al., J. Biol. Chem. 266:23060-23067 (1991)); inteferon receptor (Kurschner et al., J. Biol. Chem. 267:9354-9360 (1992)); 4-1BB (Chalupny et al., PNAS USA 89:10360-10364 (1992)) and IgE receptor (Ridgway and Gorman, J. Cell. Biol. 115, Abstract No. 1448 (1991)).

Examples of homomultimeric immunoadhesins which have been described for therapeutic use include the CD4-IgG immunoadhesin for blocking the binding of HIV to cell-surface CD4. Data obtained from Phase I clinical trials, in which CD4-IgG was administered to pregnant women just before delivery, suggests that this immunoadhesin may be useful in the prevention of maternal-fetal transfer of HIV (Ashkenazi et al., Intern. Rev. Immunol. 10:219-227 (1993). An immunoadhesin which binds tumor necrosis factor (TNF) has also been developed. TNF is a proinflammatory cytokine which has been shown to be a major mediator of septic shock. Based on a mouse model of septic shock, a TNF receptor immunoadhesin has shown promise as a candidate for clinical use in treating septic shock (Ashkenazi, A. et al. (1991) PNAS USA 88:10535-10539). ENBREL® (etanercept), an immunoadhesin comprising a TNF receptor sequence fused to an IgG Fc region, was approved by the U.S. Food and Drug Administration (FDA), on Nov. 2, 1998, for the treatment of rheumatoid arthritis. The new expanded use of ENBREL® in the treatment of rheumatoid arthritis has recently been approved by FDA on Jun. 6, 2000. For recent information on TNF blockers, including ENBREL®, see Lovell et al., N. Engl. J. Med. 342: 763-169 (2000), and accompanying editorial on p810-811; and Weinblatt et al., N. Engl. J. Med. 340: 253-259 (1999); reviewed in Maini and Taylor, Annu. Rev. Med. 51: 207-229 (2000). Immunoadhesins also have non-therapeutic uses. For example, the L-selectin receptor immunoadhesin was used as a reagent for histochemical staining of peripheral lymph node high endothelial venules (HEV). This reagent was also used to isolate and characterize the L-selectin ligand (Ashkenazi at al., supra).

If the two arms of the immunoadhesin structure have different specificities, the immunoadhesin is called a "bispecific immunoadhesin" by analogy to bispecific antibodies. Dietsch et al., J. Immunol. Methods 162:123 (1993) describe such a bispecific immunoadhesin combining the extracellular domains of the adhesion molecules, E-selectin and P-selectin, each of which selectins is expressed in a different cell type in nature. Binding studies indicated that the bispecific immunoglobulin fusion protein so formed had an enhanced ability to bind to a myeloid cell line compared to the monospecific immunoadhesins from which it was derived.

The term "heteroadhesin" is used interchangeably with the expression "chimeric heteromultimer adhesin" and refers to a complex of chimeric molecules (amino acid sequences) in which each chimeric molecule combines a biologically active portion, such as the extracellular domain of each of the heteromultimeric receptor monomers, with a multimerization domain. The "multimerization domain" promotes stable interaction of the chimeric molecules within the heteromultimer complex. The multimerization domains may interact via an immunoglobulin sequence, leucine zipper, a hydrophobic region, a hydrophilic region, or a free thiol which forms an intermolecular disulfide bond between the chimeric molecules of the chimeric heteromultimer. The multimerization domain may comprise an immunoglobulin constant region. In addition a multimerization region may be engineered such that steric interactions not only promote stable interaction, but further promote the formation of heterodimers over homodimers from a mixture of monomers. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). The immunoglobulin sequence preferably, but not necessarily, is an immunoglobulin constant domain. The immunoglobulin moiety in the chimeras of the present invention may be obtained from $IgG_1$, $IgG_2$, $IgG_3$ or $IgG_4$ subtypes, IgA, IgE, IgD or IgM, but preferably $IgG_1$ or $IgG_3$.

The term "epitope tagged" when used herein refers to a chimeric polypeptide comprising the entire chimeric heteroadhesin, or a fragment thereof, fused to a "tag polypeptide". The tag polypeptide has enough residues to provide an epitope against which an antibody can be made, yet is short enough such that it does not interfere with activity of the chimeric heteroadhesin. The tag polypeptide preferably is fairly unique so that the antibody thereagainst does not substantially cross-react with other epitopes. Suitable tag polypeptides generally have at least 6 amino acid residues and usually between about 8-50 amino acid residues (preferably between about 9-30 residues). An embodiment of the invention encompasses a chimeric heteroadhesin linked to an epitope tag, which tag is used to detect the adhesin in a sample or recover the adhesin from a sample.

"Isolated/highly purified/substantially homogenous immunoadhesin", "isolated/highly purified/substantially homogenous heteroadhesin", and "isolated/highly purified/substantially homogenous chimeric heteromultimer adhesin", are used interchangeably and mean the adhesin that has been purified from a source or has been prepared by recombinant or synthetic methods and is sufficiently free of other peptides or proteins to homogeneity by chromatographic techniques or other purification techniques, such as SDS-PAGE under nonreducing or reducing conditions using Coomassie blue or, preferably, silver stain. Homogeneity here means less than about 5% contamination with other source proteins. The ErbB2/4-IgG chimeric heteroadhesins of the invention bind with sufficiently greater affinity relative to the homodimers that the use of a mixture of homodimers and heterodimers is also considered a useful embodiment of the invention. The terms "chimeric heteromultimer adhesin", "chimeric heteroadhesin" and "CHA" are used interchangeably herein.

The term "antibody" is used in the broadest sense and specifically covers antibodies that recognize native ErbB4 receptors. An antibody that shows "high affinity" binding has a Kd of less than about 100 nM, preferably less than about 50, more preferably less than about 25, most preferably less than about 10.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-chimeric heteroadhesin antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, $F(ab)_2$, and Fv), so long as they exhibit the desired biological activity. (See, e.g., U.S. Pat. No. 4,816,567 and Mage & Lamoyi, in *Monoclonal Antibody Production Techniques and Applications*, pp. 79-97 (Marcel Dekker, Inc.), New York (1987)).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, Nature 256:495 (1975), or may be made by recombinant DNA methods (U.S. Pat. No. 4,816,567). The "monoclonal antibodies" may also be isolated from phage libraries generated using the techniques described in McCafferty et al, Nature 348:552-554 (1990), for example.

"Humanized" forms of non-human (e.g. murine) antibodies are specific chimeric immunoglobulins, immunoglobulin chains or fragments thereof (such as Fv, Fab, Fab', $F(ab)_2$ or other antigen-binding subsequences of antibodies) which contain minimal sequence derived from non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

"Muscle cells" include skeletal, cardiac or smooth muscle tissue cells. This term encompasses those cells which differentiate to form more specialized muscle cells (e.g. myoblasts). Vascular smooth muscle cells refer to smooth muscle cells present in a middle elastic layer, media, of blood vessels.

The term "stenosis" refers to narrowing or stricture of a hollow passage (e,g, a duct or canal) in the body. The term "vascular stenosis" refers to occlusion or narrowing of blood vessels. Vascular stenosis often results from fatty deposit (as in the case of atherosclerosis) or excessive migration and proliferation of vascular smooth muscle cells and endothelial cells. Arteries are particularly susceptible to stenosis. The term "stenosis" as used herein specifically includes initial stenosis and restenosis.

The term "restenosis" refers to recurrence of stenosis after treatment of initial stenosis with apparent success. For example, "restenosis" in the context of vascular stenosis, refers to the reoccurrence of vascular stenosis after it has been treated with apparent success, e.g. by removal of fatty deposit by balloon angioplasty. One of the contributing factors in restenosis is intimal hyperplasia. The term "intimal hyperplasia", used interchangeably with "neointimal hyperplasia" and "neointima formation", refers to thickening of the inner most layer of blood vessels, intima, as a consequence of excessive proliferation and migration of vascular smooth muscle cells and endothelial cells. The various changes taking place during restenosis are often collectively referred to as "vascular wall remodeling."

The terms "balloon angioplasty" and "percutaneous transluminal coronary angioplasty" (PTCA) are often used interchangeably, and refer to a non-surgical catheter-based treatment for removal of plaque from the coronary artery. Stenosis or restenosis often lead to hypertension as a result of increased resistance to blood flow.

The term "pyloric stenosis" refers to narrowing of pylorus, the passage at the lower end of the stomach that opens into the duodenum.

The term "hypertension" refers to abnormally high blood pressure, i.e. beyond the upper value of the normal range.

By "neutralizing antibody" is meant an antibody molecule as herein defined which is able to block or significantly reduce an effector function of ErbB receptors. Accordingly, a "neutralizing" anti-ErbB4 antibody is capable of blocking or significantly reducing an effector function, such as ligand binding and/or elicitation of a cellular response, of ErbB4. For the purpose of the present invention, the ability of an anti-ErbB4 antibody to neutralize the binding of an ErbB4 ligand (heregulin, HRG) to ErbB4 can be monitored, for example, by measuring the binding of detectably labeled HRG to purified ErbB4 or to a cell line exressing or modified to express ErbB4 in the presence and absence of a candidate anti-ErbB4 antibody. Such assays are described in Example 4 below. For the purpose of the present invention, the ability of the anti-ErbB4 antibodies to neutralize the elicitation of a cellular response by ErbB4 is preferably tested by monitoring the inhibition of tyrosine phosphorylation of ErbB4 by heregulin (HRG), or in a cell proliferation assay. Representative assays are disclosed in Example 4 below. "Significant" reduction means at least about 60%, or at least about 70%, preferably at least about 75%, more preferably at least about 80%, even more preferably at least about 85%, still more preferably at least about 90%, still more preferably at least about 95%, most preferably at least about 99% reduction of an effector function of the target antigen (e.g. ErbB4), such as ligand (e.g. HRG) binding and/or elicitation of a cellular response. Preferably, the "neutralizing" antibodies as defined herein will be capable of neutralizing at least about 60%, or at least about 70%, preferably at least about 75%, more preferably at least about 80%; even more preferably at least about 85%, still more preferably at least about 90%, still more preferably at least about 95%, most preferably at least about 99% of the tyrosine phosphorylation of ErbB4 by HRG, as determined by the assay described in Example 4.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SOS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope" is used to refer to binding sites for (monoclonal or polyclonal) antibodies on protein antigens.

Antibodies which bind to a particular epitope can be identified by "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. Competition assays are discussed below. According to the gene fragment expression assays, the open reading frame encoding the protein is fragmented either randomly or by specific genetic constructions and the reactivity of the expressed fragments of the protein with the antibody to be tested is determined. The gene fragments may, for example, be produced by PCR and then transcribed and translated into protein in vitro, in the presence of radioactive amino acids. The binding of the antibody to the radioactively labeled protein fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. The latter approach is suitable to define linear epitopes of about 5 to 15 amino acids.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The phrase "inhibiting an ErbB4 (HER4) receptor" refers to the ability of an ErbB4 antagonist to inhibit or prevent activation of an ErbB4 receptor, for example, by blocking the binding of a ligand to the ErbB4 receptor. The "activation" of an ErbB4 receptor refers to receptor phosphorylation, which can be quantified using the tyrosine phosphorylation assays, and downstream events that constitute induction of signal transduction by the bound ligand. "Inhibition" is any of these assays is at least about 60%, or at least about 70%, preferably at least about 75%, more preferably at least about 80%; even more preferably at least about 85%, still more preferably at least about 90%, still more preferably at least about 95%, most preferably at least about 99%.

The expression "decreasing survival of a cell" refers to the act of decreasing the period of existence of a cell, relative to an untreated cell which has not been exposed to a ErbB4 antagonist either in vitro or in vivo. The expression "decreased cell proliferation" refers to a decrease in the number of cells in a population exposed to an ErbB4 antagonist either in vitro or in vivo, relative to an untreated cell.

"Biological activity" where used in conjunction with an ErbB4 antagonist refers to the ability of an ErbB4 antagonist to control the excessive proliferation or migration of smooth muscle cells, as determined in a relevant in vitro or in vivo assay, including the PDGF-stimulated smooth muscle cell proliferation and human aortic smooth muscle cell migration assays described in the Examples hereinbelow, animal models and human clinical trials, irrespective of the underlying mechanism. Thus, the biological activity of an ErbB4 antagonist includes, without limitation, functioning as an inhibitor of the binding of a ligand or activation of a native ErbB4 receptor, and/or inhibition of growth and/or migration of smooth muscle cells expressing an ErbB4 receptor on their surface.

The term "disease state" refers to a physiological state of a cell or of a whole mammal in which an interruption, cessation, or disorder of cellular or body functions systems, or organs has occurred.

The term "effective amount" refers to an amount of a drug effective to treat (including prevention) a disease, disorder or unwanted physiological conditions in a mammal. In the present invention, an "effective amount" of an ErbB4 antagonist may reduce, slow down or delay the proliferation of smooth muscle cells; reduce, slow down or delay the migration of smooth muscle cells; prevent or inhibit (i.e., slow to some extent and preferably stop) the development of stenosis or restenosis; and/or relieve to some extent one or more of the symptoms associated with stenosis or restenosis, in particular, prevent or inhibit (e., slow to some extent and preferably stop) the development of elevated blood pressure associated with stenosis or restenosis.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. It such sites do not exist, the synthetic oligonucleotide adapters or linkers are used in accordance with conventional practice.

"Pharmaceutically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, polyethylene glycol (PEG), and Pluronics.

B. Methods for Carrying Out the Invention

The invention concerns the treatment of stenosis by antagonists of native ErbB4 receptors. Although the invention is not so limited, in a preferred embodiment, the antagonist is an immunoadhesin or a chimeric heteromultimer adhesin. Immunoadhesins (referred to as hybrid immunoglobulins), including their structure and preparation, are described, e.g. in WO 91/08298; and in U.S. Pat. Nos. 5,428,130 and 5,116,964, the disclosures of which are hereby expressly incorporated by reference.

1. Production of an Immunoadhesin or Chimeric Heteromultimer Adhesin.

The description below relates primarily to production of immunoadhesin by culturing cells transformed or transfected with a vector containing immunoadhesin nucleic acid. It is, of course, contemplated that alternative methods, which are well known in the art, may be employed to prepare immunoadhesin. For instance, the immunoadhesin sequence, or portions thereof, may be produced by direct peptide synthesis using solid-phase techniques [see, e.g., Stewart et al., *Solid-Phase Peptide Synthesis,* W.H. Freeman Co., San Francisco, Calif. (1969); Merrifield, *J. Am. Chem. Soc.,* 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the immunoadhesin may be chemically synthesized separately and combined using chemical or enzymatic methods to produce the full-length immunoadhesin.

Nucleic acid encoding a native sequence ErbB4 receptor can, for example, be isolated from cells known to express the ErbB4 receptor, such as those described in EP 599,274, supra, and in the collective Plowman et al. references, supra or is synthesized.

DNA encoding immunoglobulin light or heavy chain constant regions is known or readily available from cDNA libraries or is synthesized. See for example, Adams et al., Biochemistry 19:2711-2719 (1980); Gough et al., Biochemistry 19:2702-2710 (1980); Dolby et al; P.N.A.S. USA, 77:6027-6031 (1980); Rice et al P.N.A.S USA 79:7862-7865 (1982); Falkner et al; Nature 298:286-288 (1982); and Morrison et al; Ann. Rev. Immunol. 2:239-256 (1984).

An immunoadhesin or a chimeric heteroadhesin of the invention is preferably produced by expression in a host cell and isolated therefrom. A host cell is generally transformed with the nucleic acid of the invention. Preferably the nucleic acid is incorporated into an expression vector. Suitable host cells for cloning or expressing the vectors herein are prokaryote host cells (such as *E. coli*, strains of *Bacillus, Pseudomonas* and other bacteria), yeast and other eukaryotic microbes, and higher eukaryote cells (such as Chinese hamster ovary (CHO) cells and other mammalian cells). The cells may also be present in live animals (for example, in cows, goats or sheep). Insect cells may also be used. Cloning and expression methodologies are well known in the art.

To obtain expression of an immunoadhesin such as a chimeric ErbB4-IgG molecule, one or more expression vector(s) is/are introduced into host cells by transformation or transfection and the resulting recombinant host cells are cultured in conventional nutrient media, modified as appropriate for inducing promoters, selecting recombinant cells, or amplifying the ErbB4-IgG DNA. In general, principles, protocols, and practical techniques for maximizing the productivity of in vitro mammalian cell cultures can be found in *Mammalian Cell Biotechnology: a Practical Approach*, M. Butler, ed. (IRL Press, 1991).

(i) Construction of Nucleic Acid Encoding Immunoadhesin

When preparing the immunoadhesins of the present invention, preferably nucleic acid encoding an extracellular domain of a natural receptor is fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The resultant DNA fusion construct is expressed in appropriate host cells.

Nucleic acid molecules encoding amino acid sequence variants of native sequence extracellular domains (such as from ErbB4) and/or the antibody sequences used to prepare the desired immunoadhesin, are prepared by a variety of methods known in the art. These methods include, but are not limited to, isolation from a natural source (in the case of naturally occurring amino acid sequence variants, such as those mentioned above in connection with ErbB4) or preparation by oligonucleotide-mediated (or site-directed) mutagenesis, PCR mutagenesis, and cassette mutagenesis of an earlier prepared variant or a non-variant version of native sequence ErbB4.

Amino acid sequence variants of native sequence extracellular domain included in the chimeric heteroadhesin are prepared by introducing appropriate nucleotide changes into the native extracellular domain DNA sequence, or by in vitro synthesis of the desired chimeric heteroadhesin monomer polypeptide. Such variants include, for example, deletions from, or insertions or substitutions of, residues in the amino acid sequence of the immunoadhesin or chimeric heteroadhesin.

Variations in the native sequence as described above can be made using any of the techniques and guidelines for conservative and non-conservative mutations set forth in Table 1.

In a preferred embodiment, the nucleic acid encodes a chimeric molecule in which the ErbB4 receptor extracellular domain sequence is fused to the N-terminus of the C-terminal portion of an antibody (in particular the Fc domain), containing the effector functions of an immunoglobulin, e.g. IgG1. It is possible to fuse the entire heavy chain constant region to the ErbB4 receptor extracellular domain sequence. However, more preferably, a sequence beginning in the hinge region just upstream of the papain cleavage site (which defines IgG Fc chemically; residue 216, taking the first residue of heavy chain constant region to be 114 [Kobet et al., supra], or analogous sites of other immunoglobulins) is used in the fusion. In a particularly preferred embodiment, the ErbB4 receptor extracellular domain sequence is fused to the hinge region and CH2 and CH3 or CH1, hinge, CH2 and CH3 domains of an IgG1, IgG2, or IgG3 heavy chain. The precise site at which the fusion is made is not critical, and the optimal site can be determined by routine experimentation.

For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger "adhesin" domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit.

For ErbB4-Ig immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in viva half-life in approximately one third of the other IgG isotypes.

Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one of these sites G1m1, is non-immunogenic. In contrast, there are 12 serologically-defined allotypes in IgG3, all of which are in the Fc region; only three of these sites (G3 m5, 11 and 21have one allotype which is nonimmunogenic. Thus, the potential immunogenicity of an IgG3 immunoadhesin is greater than that of an IgG1 immunoadhesin.

The cDNAs encoding the ErbB4 receptor sequence (e.g. an extracellular domain sequence) and the Ig parts of the immunoadhesin are inserted in tandem into a plasmid vector that directs efficient expression in the chosen host cells. For expression in mammalian cells pRK5-based vectors [Schall et al., Cell 61, 361-370 (1990)] and CDM8-based vectors [Seed, Nature 329, 840 (1989)] may, for example, be used. The exact junction can be created by removing the extra sequences between the designed junction codons using of oligonucleotide-directed deletional mutagenesis [Zoller and Smith, Nucleic Acids Res. 10, 6487 (1982); Capon et al., Nature 337, 525-531 (1989)]. Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

Although the presence of an inmmnoglobulin light chain is not required in the immunoadhesins of the present invention, an immunoglobulin light chain might be present either covalently associated to an trk receptor-in-irnunoglobulin heavy chain fusion polypeptide, or directly fused to the trk receptor extracellular domain. In the former case, DNA encoding an immunoglobulin light chain is typically coexpressed with the DNA encoding the ErbB4 receptor-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Method suitable for the preparation of such structures are, for example, disclosed in U.S. Pat. No. 4,816,567 issued Mar. 28, 1989.

Another preferred type of chimeric ErbB4 antagonist herein is a fusion protein comprising an extracellular domain, such as from a ErbB4 monomer, linked to a heterologous polypeptide, such as a multimerization domain. Such a sequence can be constructed using recombinant DNA techniques. Alternatively, the heterologous polypeptide can be covalently bound to the extracellular domain polypeptide by techniques well known in-the art such as the use of the heterobifunctional crosslinking reagents. Exemplary coupling agents include N-succinimidyl-3-(2-pyridyidithiol) propionate (SPDP), iminothiolane (IT), bifunctional derivatives of imidoesters (such as dimethyl adipimidate HCLC, active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

In one embodiment, a chimeric heteroadhesin polypeptide comprises a fusion of a monomer of the chimeric heteroadhesin with a tag polypeptide which provides an epitope to which an anti-tag antibody can selectively bind. Such epitope tagged forms of the chimeric heteroadhesin are useful, as the presence thereof can be detected using a labeled antibody against the tag polypeptide. Also, provision of the epitope tag enables the chimeric heteroadhesin to be readily purified by affinity purification using the anti-tag antibody. Tag polypeptides and their respective antibodies are well known in the art. Examples include the flu HA tag polypeptide and its antibody 12CA5, (Field et al., Mol. Cell. Biol. 8:2159-2165 (1988)); the c-myc tag and the 8F9, 3C7, 6E10, G4, B7 and 9E10 antibodies thereto (Evan et al., Molecular and Cellular Biology 5(12):3610-3616 (1985)); and the Herpes Simplex virus glycoprotein D (gD) tag and its antibody (Paborsky et al., Protein Engineering 3(6):547-553 (1990)).

Another type of covalent modification of a chimeric heteromultimer comprises linking a monomer polypeptide of the heteromultimer to one of a variety of non-proteinaceous polymers, e.g., polyethylene glycol, polypropylene glycol, polyoxyalkylenes, or copolymers of polyethylene glycol and polypropylene glycol. A chimeric heteromultimer also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

(ii) Selection and Transformation of Host Cells

Host cells are transfected or transformed with expression or cloning vectors described herein for immunoadhesin production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

The terms "transformation" and "transiection" are used interchangeably herein and refer to the process of introducing DNA into a cell. Following transformation or transfection, the nucleic acid of the invention may integrate into the host cell genome, or may exist as an extrachromosomal element. Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as Escherichia, e.g., *E. coli Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentation. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan'; *E. coli* W3110 strain 37D6, which has the complete genotype tonA ptr3phoA E15 (argF-lac)169 degP ompT rbs 7 ilvG kan'; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for immunoadhesin-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2):737-1742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans,* and *K. marxianus; yarrowia* (EP 402,226); *Pichia pastoris* (EP 183,070; Sreekrishna et al., *J. Basi Microbiol.,* 28:265-278 [1998)); Candida; *Trichoderma reesia* (EP 244,234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published Jan. 10, 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula.* A list of specific species that are exemplary of this class of yeasts may be found in C. Anthony, *The Biochemistry of Methylotrophs,* 269 (1982).

Suitable host cells for the expression of glycosylated immunoadhesin are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651): human embryonic kidney line (293 or 293 cells subcloned for growth in suspension culture, Graham et al., *J. Gen Virol.,* 36:59 (1977)); Chinese hamster ovary cells/-DHFR(CHO, Urlaub and Chasin, *Proc. Natl. Acad. Sci. USA,* 77:4216 (1980)); mouse sertali cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

In general, the choice of a mammalian host cell line for the expression of ErbB4-Ig immunoadhesins depends mainly on the expression vector (see below). Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method [Aruffo et al., Cell 61, 1303-1313 (1990)]; Zettmeissl et al., DNA Cell Biol. (US) 9, 347-353 (1990)]. If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts [Gascoigne et al., 1987, supra; Martin et al., J. Virol. 67, 3561-3568 (1993)].

(iii) Selection and Use of a Replicable Vector

The nucleic acid encoding immunoadhesin may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The immunoadhesin may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the immunoadhesin-encoding DNA that is inserted into the vector. The signal sequence may be a prokaryotic signal sequence selected, for example, from the group of the alkaline phosphatase, penicillinase, Ipp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the immunoadhesin-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsma et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the immunoadhesin-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,7761], and hybrid promoters such as the tac promoter [deBoer et al., *Proc. Natl. Acad. Sci. USA*, 80:21-25 (1983)]. Promoters for use in bacterial systems also wil contain a Shine-Dalgarno (S.D.) sequence operably linked to the DNA encoding immunoadhesin.

Examples of suitable promoter sequences for use with yeast hosts include the promoters for 3-phosphoglycerate kinase [Hitzeman et al., *J. Biol. Chem.*, 255:2073 (1980)] or other glycolytic enzymees [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

The transcription of immunoadhesin from vectors in mammalian host cells is controlled, for example, by promoters obtained from the genomes of viruses such as polyoma virus, fowlpox virus (UK 2,211,504 published 5 Jul. 1989), adenovirus (such as Adenovinus 2), bovine papilloma virus, retrovirus (such as avian sarcoma virus), cytomegalovirus, hepatitis-B virus and Simian Virus 40 (SV40); from heterologous mammalian promoters, e.g., the actin promoter or an immunoglobulin promoter, or from heat-shock promoters, provided such promoters are compatible with the host cell systems.

Transcription of a DNA encoding the immunoadhesin by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (by 100-270), the cytomegalovirus early promoter enhancer, the polyoma enhancer on the late side of the replication origin, and adenovirus enhancers. The enhancer may be spliced into the vector at a position 5' or 3' to the immunoadhesin coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 3' untranslated regions of eukaryotic or viral DNAs or cDNAs. These regions contain nucleotide segments transcribed as polyadenylated fragments in the untranslated portion of the mRNA encoding immunoadhesin.

Still other methods, vectors, and host cells suitable for adaptation to the synthesis of immunoadhesin in recombinant vertebrate cell culture are described in Gething et al., *Nature*, 293:620-625 (1981); Mantei et al., *Nature*, 281:40-46 (1979); EP 117,060; and EP 117,058.

(iv) Purification of Immunoadhesin

An immunoadhesin or a chimeric heteroadhesin preferably is recovered from the culture medium as a secreted polypeptide, although it also may be recovered from host cell lysates. As a first step, the particulate debris, either host cells or lysed fragments, is removed, for example, by centrifugation or ultrafiltration; optionally, the protein may be concentrated with a commercially available protein concentration filter, followed by separating the chimeric heteroadhesin from other impurities by one or more purification procedures selected from: fractionation on an immunoaffinity column; fractionation on an ion-exchange column; ammonium sulphate or ethanol precipitation; reverse phase HPLC; chromatography on silica; chromatography on heparin Sepharose; chromatography on a cation exchange resin; chromatofocusing; SDS-PAGE; and gel filtration.

A particularly advantageous method of purifying immunoadhesins is affinity chromatography. The choice of affinity ligand depends on the species and isotype of the immunoglobulin Fc domain that is used in the chimera. Protein A can be used to purify immunoadhesins that are based on human IgG1, IgG2, or IgG4 heavy chains [Lindmark et al., J. Immunol. Meth. 62, 1-13 (1983)]. Protein G is recommended for all mouse isotypes and for human IgG3 [Guss et al., EMBO J. 5, 1567 1575 (1986)]. The matrix to which the affinity ligand is attached is most often agarose, but other matrices are also available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human IgG1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography [Hutchens and Porath, Anal. Biochem. 159, 217-226 (1986)] and immobilized metal chelate chromatography [AI-Mashikhi and Makai, J. Dairy Sci. 71, 1756-1763 (1988)]. In contrast to antibodies, however, their behavior on ion exchange columns is dictated not only by their isoelectric points, but also by a charge dipole that may exist in the molecules due to their chimeric nature.

Preparation of epitope tagged immunoadhesin, such as ErbB4-IgG, facilitates purification using an immunoaffinity column containing antibody to the epitope to adsorb the fusion polypeptide. Immunoaffinity columns such as a rabbit polyclonal anti-ErbB4 column can be employed to absorb the ErbB4-IgG by binding it to an ErbB4 immune epitope.

In some embodiments, the ErbB4 receptor-immunoglobulin chimeras (immunoadhesins) are assembled as monomers, or hetero- or homo-multimers, and particularly as dimers or tetramers, essentially as illustrated in WO 91/08298. Generally, these assembled immunoglobulins will have known unit structures. A basic four chain structural unit is the form in which Ig, IgD, and IgE exist. A four-unit structure is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

As noted earlier, the immunoadhesins of the present invention can be made bispecific, and may, for example, include binding regions from two different ErbB receptors, at least one or which is ErbB4. Thus, the immunoadhesins of the present invention may have binding specificities for two distinct ErbB ligands. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

(v) Characterization of Immunoadhesin

Generally, the ErbB4 chimeric heteromultimers of the invention will have any one or more of the following properties: (a) the ability to compete with a natural heteromultimeric receptor for binding to a ligand such as HB-EGF; (b) the ability to form ErbB2-IgG/ErbB4-IgG complexes; and (c) the ability to inhibit activation of a natural heteromultimeric receptor by depleting ligand from the environment of the natural receptor, thereby inhibiting proliferation of cells that express the ErbB2 and ErbB4 receptor.

To screen for property (a), the ability of the chimeric ErbB4 heteromultimer adhesin to bind to a ligand can be readily determined in vitro. For example, immunoadhesin forms of these receptors can be generated and the ErbB2/4-Ig heteroimmunoadhesin can be immobilized on a solid phase (e.g. on assay plates coated with goat-anti-human antibody). The ability of a ligand to bind to the immobilized immunoadhesin can then be determined. For more details, see the $^{125}$I-HRG binding assay described in the Example below.

As to property (c), the tyrosine phosphorylation assay using MCF7 cells provides a means for screening for activation of ErbB4 receptors. In an alternative embodiment of the invention, the KIRA-ELISA described in WO 95/14930 can be used to qualitatively and quantitatively measure the ability of an HER4 chimeric heteroadhesin to inhibit activation of a HER4 receptor.

The ability of an immunoadhesin, chimeric heteroadhesin such as ErbB2/4-Ig, or other molecule of the present invention to inhibit proliferation of a cell that expresses the ErbB2 and ErbB4 receptor is readily determined in cell culture by standard procedures. Useful cells for this experiment include MCF7 and SK-BR-3 cells obtainable from the ATCC and Schwann cells (see, for example, Li et al., J. Neuroscience 16(6):2012-2019 (1996)). These tumor cell lines may be plated in cell culture plates and allowed to adhere thereto. The HRG ligand in the presence and absence of a potential ErbB4 antagonist such as an ErbB4 chimeric heteroadhesin is added. Monolayers are washed and stained/fixed with crystal violet and cell growth inhibition is quantified.

2. Antibody Preparation

Another preferred class of ErbB4 antagonists comprises neutralizing antibodies to this receptor.

(i) Polyclonal Antibodies

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

(ii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103, [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and MC.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63, Marcel Dekker, Inc., New York, [1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp. 59-103 (Academic Press, 1986)). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-ErbB4 receptor monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a ErbB4 receptor and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Recombinant production of antibodies will be described in more detail below.

(iii) Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody.

Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details, see U.S. Pat. No. 5,821,337.

(iv) Human Antibodies

Human monoclonal antibodies can be made by the hybridoma method. Human myeloma and mouse-human heteromyeloma cell lines for the production of human monoclonal antibodies have been described, for example, by Kozbor, *J. Immunol.* 133, 3001 (1984), and Brodeur, et al, *Monoclonal Antibody Production Techniques and Applications*, pp. 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551-255 (1993); Jakobovits et al., *Nature* 362, 255-258 (1993).

Mendez at al. (*Nature Genetics* 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions ($\mu$, $\delta$ and $\chi$), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, the phage display technology (McCafferty et al., *Nature* 348, 552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., *Current Opinion in Structural Biology* 3, 564-571 (1993). Several sources of V-gene segments can be used for phage display. Clackson et al., *Nature* 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al, *J. Mol. Biol.* 222, 581-597 (1991), or Griffiths et al., *EMBO J.* 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al., *Nucl. Acids Res.* 21, 2265-2266 (1993), and the isolation of a high affinity human antibody directly from such large phage library is reported by Griffiths et al., *EMBO J.* 13: 3245-3260 (1994). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable domains capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

(i) Bispecific Antibodies

Bispecific antibodies are monoclonal, preferably human or humanized, antibodies that have binding specificities for at least two different antigens. In the present case, one of the binding specificities is for the ErbB4 receptor to provide an antagonist antibody, the other one is for any other antigen, and preferably for another receptor or receptor subunit.

Methods for making bispecific antibodies are known in the art. Traditionally, the recombinant production of bispecific antibodies is based on the co-expression of two immunoglobulin heavy chain-light chain pairs, where the two heavy chains have different specificities (Millstein and Cuello, *Nature* 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO93/08829 (published 13 May 1993), and in Traunecker et al., *EMBO* 10, 3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation.

For further details of generating bispecific antibodies see, for example, Suresh et al., *Methods in Enzymology* 121, 210 (1986).

(vi) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

(vii) Antibody Fragments

In certain embodiments, the ErbB4 antagonist antibody (including murine, human and humanized antibodies, and antibody variants) is an antibody fragment. Various techniques have been developed for the production of antibody fragments. Traditionally, these fragments were derived via proteolytic digestion of intact antibodies (see, e.g., Morimoto at al., *J. Biochem. Biophys. Methods* 24:107-117 (1992) and Brennan et al., *Science* 229:81 (1985)). However, these fragments can now be produced directly by recombinant host cells. For example, Fab'-SH fragments can be directly recovered from *E. coli* and chemically coupled to form F(ab')$_2$ fragments (Carter et al., *Bio/Technology* 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

(viii) Amino Acid Sequence Variants of Antibodies

Amino acid sequence variants of the ErbB4 antagonist antibodies are prepared by introducing appropriate nucleotide changes into the ErbB4 antagonist antibody DNA, or by peptide synthesis. Such variants include, for example, deletions from, and/or insertions into and/or substitutions of, residues within the amino acid sequences of the ErbB4 antagonist antibodies of the examples shown herein. Any combination of deletion, insertion, and substitution is made to arrive at the final construct, provided that the final construct possesses the desired characteristics. The amino acid changes also may alter post-translational processes of the humanized or variant ErbB4 antagonist antibody, such as changing the number or position of glycosylation sites.

A useful method for identification of certain residues or regions of the ErbB4 receptor antibody that are preferred locations for mutagenesis is called "alanine scanning mutagenesis," as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with ErbB4 receptor antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed ErbB4 antibody variants are screened for the desired activity.

Amino acid sequence insertions include amino and/or carboxy-terminal fusions ranging in length from one residue to polypeptides containing a hundred or more residues, as well as intrasequence insertions of single or multiple amino acid residues. Examples of terminal insertions include a ErbB4 antagonist antibody with an N-terminal methionyl residue or the antibody fused to an epitope tag. Other insertional variants of the ErbB4 antagonist antibody molecule include the fusion to the N- or C-terminus of the ErbB4 antagonist antibody of an enzyme or a polypeptide which increases the serum half life of the antibody.

Another type of variant is an amino acid substitution variant. These variants have at least one amino acid residue in the ErbB4 antagonist antibody molecule removed and a different residue inserted in its place. The sites of greatest interest for substitution mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | Tyr; phe | tyr |
| Tyr (Y) | Trp; phe; thr; ser | phe |
| Val (V) | Ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the ErbB4 antagonist antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as a Fv fragment).

A particularly preferred type of substitution variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitution variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. antagonist activity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and ErbB receptor. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except praline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the ErbB4 antagonist antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the ErbB4 antagonist antibody.

(ix) Other Modifications of Antibodies

The ErbB4 antagonist antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286-288 (1982) via a disulfide interchange reaction. A chemotherapeutic agent (such as Doxorubicin) is optionally contained within the liposome. See Gabizon et al, *J. National Cancer Inst.* 81(19):1484 (1989).

The antibody of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as—galactosidase and neuraminidase useful for converting glycosylated prodrugs into free drugs; —lactamase useful for converting drugs derivatized with—lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the ErbB4 antagonist antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 [1984]).

In certain embodiments of the invention, it may be desirable to use an antibody fragment, rather than an intact antibody. In this case, it may be desirable to modify the antibody fragment in order to increase its serum half-life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO96/32478 published 17 Oct. 1996.

The salvage receptor binding epitope generally constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

Covalent modifications of the ErbB4 antagonist antibodies are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

3. Preparation of Soluble ErbB4 Receptors

Soluble ErbB4 receptors, such an ErbB4 extracellular domain, can be prepared by culturing cells transformed or transfected with a vector containing the encoding nucleic acid. It is, of course, contemplated that alternative methods, which are well known in the art, may be employed to prepare such soluble receptors. For instance, the soluble receptor sequence, or portions thereof, may be produced by direct peptide synthesis using solid-phase techniques (see, e.g., Stewart et al., supra; and Merrifield, supra). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the soluble receptor may be chemically synthesized separately and combined using chemical or enzymatic methods to produce the full-length soluble receptor.

Recombinant production of soluble ErbB4 receptors is performed essentially as described hereinabove in connection with immunoadhesins.

The most convenient method for the large-scale production of soluble ErbB4 receptors is by cleavage from an ErbB4-Ig immunoadhesin. The structural similarity between immunoadhesins and antibodies suggested that it might be possible to cleave immunoadhesins by proteolytic enzymes such as papain, to generate Fd-like fragments containing the "adhesin" portion. In order to provide a more generic approach for cleavage of immunoadhesins, proteases which are highly specific for their target sequence are to be used. A protease suitable for this purpose is an engineered mutant of subtilisin BPN, which recognizes and cleaves the sequence AAHYTL. Introduction of this target sequence into the support hinge region of an ErbB4-IgG (e.g. IgG1) immunoadhesin facilitates highly specific cleavage between the Fc and trk domains. The IgG1 immunoadhesin is purified by protein A chromatography and cleaved with an immobilized form of the enzyme. Cleavage results in two products; the Fc region and the ErbB4 region, which is preferably an ErbB4 extracellular domain. These fragments can be separated easily by a second passage over a protein A column to retain the Fc and obtain the purified ErbB4 fragment in the flow-through fractions. A similar approach can be used to generate a dimeric ErbB4 portion, by placing the cleavable sequence at the lower hinge.

4. Therapeutic Compositions and Methods

The members of the ErbB family of receptors and corresponding ligands are involved in smooth muscle cell proliferation in various organs. Accordingly, an ErbB4 receptor antagonist may be utilized for the treatment of a variety of "diseases or disorders" involving smooth muscle cell proliferation in a mammal, such as a human.

In a preferred embodiment, the present invention concerns the use of ErbB4 receptor antagonists for the treatment of cardiac diseases involving proliferation of vascular smooth muscle cells (VSMC) and leading to intimal hyperplasia such as vascular stenosis, restenosis resulting from angioplasy or surgery or stent implants, atherosclerosis and hypertension (reviewed in Casterella and Teirstein, *Cardiol. Rev.* 7: 219-231 [1999]; Andres, *Int. J. Mol. Med.* 2: 81-89 [1998]; and Rosanio et al., *Thromb Haemost.* 82 [suppl 1]: 164-170 [1999]). There is an intricate interplay of various cells and cytokines released that act in autocrine, paracrine or juxtacrine manner, which result in migration of VSMCs from their normal location in media to the damaged intima. The migrated VSMCs proliferate excessively and lead to thickening of intima, which results in stenosis or occlusion of blood vessels. The problem is compounded by platelet aggregation and deposition at the site of lesion. α-thrombin, a multifunctional serine protease, is concentrated at site of vascular injury and stimulates VSMCs proliferation. Following activation of this receptor, VSMCs produce and secrete various autocrine growth factors, including PDGF-AA, HB-EGF and TGF-β (reviewed in Stouffer and Runge, *Semin. Thromb. Hemost.* 24: 145-150 [1998]).

Various members of the EGF family play important roles in the normal growth and maintenance of blood vessels as well as in pathological conditions. For example, heparin-binding EGF-like growth factor (HB-EGF) is a potent mitogen and a chemotactic factor for fibroblasts as well as VSMCs but not endothelial cells (reviewed in Raab and Klagsbrun, *Biochim. Biophys. Acta* 1333: F179-199 [1997]). Vascular endothelial growth factor (VEGF), a powerful angiogenic factor, induces the expression of HB-EGF in vascular endothelial cells (Arkonac et al., *J. Biol. Chem.* 273: 4400-4405 [1998]). HB-EGF binds to and activates HER1 and ErbB4 receptors initiating a signal transduction cascade that ultimately results in migration and proliferation of fibroblasts and VSMCs. HB-EGF also stimulates VSMCs to secrete various factors that are mitogenic for endothelial cells (Abramovitch at al., *FEBS Lett.* 425: 441-447 [1998]). Moreover, it also induces chemotactic response in endothelial cells. Similarly, another ligand that activates EGF receptors, epiregulin, is secreted by VSMCs stimulated with angiotensin II, endothelin-1 and thrombin, and also acts as a powerful mitogen for proliferation of VSMCs (Taylor et al., *Proc. Natl. Acad. Sci. USA* 96: 1633-1638 [1999]).

Vascular stenosis gives rise to hypertension as a result of increased resistance to blood flow. Moreover, decreased blood supply to the tissue may also cause necrosis and induce inflammatory response leading to severe damage. For example, myocardial infarction occurs as a result of lack of oxygen and local death of heart muscle tissues. Percutaneous transluminal coronary angioplasy (PTCA), simply referred to as balloon angioplasty, is a non-surgical catheter-based treatment for obstructive coronary artery disease. In this method, a catheter is introduced in the blood vessel and a balloon is inflated at the site of plaque in order to mechanically dislodge the plaque. Alternatively, stent is implanted to restore smooth blood flow. However, neointimal formation takes place even within the implanted stent, known as "in-stent restenosis." For example, stent deployment results in early thrombus deposition and acute inflammation, granulation tissue development, and ultimately smooth muscle cell proliferation and extracellular matrix synthesis (reviewed in Virmani and Farb, *Curr. Opin. Lipidol.* 10: 499-506 [1999]). Bypass surgery is performed to get around the affected blood vessel only in severe cases, and usually only after multiple rounds of angioplasty have failed in restoring blood flow.

Although balloon angioplasty has been used widely for the treatment of stenosis, its long-term success is limited by restenosis. Restenosis persists as the limiting factor in the maintenance of vessel patency after PTCA, occurring in 30-50% of patients and accounting for significant morbidity and health care expenditure. The underlying mechanisms of restenosis are comprised of a combination of effects from vessel recoil, negative vascular remodeling, thrombus formation and neointimal hyperplasia. Importantly, these events are interconnected. For example, neointimal hyperplasia is stimulated by growth factors, which are released by local thrombi and the injured arterial segment itself, and act to enhance the expression of other growth-stimulating proteins resulting in acute proliferative and inflammatory responses. For instance, endothelial injury induces expression of EGF, EGF-like factors and EGFR in VSMCs, which act upon them in an autocrine manner to stimulate their proliferation leading to intimal thickening and restenosis. Extracellular matrix (ECM) formation and accumulation in the vessel wall is another important component of the restenosis lesion that develops after balloon angioplasty.

A multitude of pharmacological trials have been conducted in an attempt to prevent restenosis, but most have demonstrated little benefits. Early clinical trials in restenosis prevention using various revascularization devices, anti-platelet drugs, anti-thrombotic drugs and anti-inflammatory drugs were uniformly negative (reviewed in Casterella and Teirstein, *Cardiol. Rev.* 7: 219-231 [1999]; Andres, *Int. J. Mol. Med.* 2: 81-89 [1998]; and Rosanio et al., *Thromb. Haemost.* 82 [suppl 1]: 164-170 [1999]). Inspite of all the recent progress, there is still no satisfactory treatment for stenosis or prevention of restenosis after balloon angioplasty or stent implantation. Although limited success has been achieved in small randomized trials, stenosis, and particularly restenosis, remains a major clinical problem. The instant invention discloses the use of ErbB4 receptor antagonists for the treatment of stenosis or restenosis by controlling the proliferation of vascular smooth muscle cells.

The scope of the present invention, however, is not restricted to the disorders of the vascular smooth muscle cells. The scope specifically includes any disorder that results from proliferation of smooth muscle cells in any organ and that involves an active role of ErbB4 receptors and/or corresponding ligands.

Infantile hypertrophic pyloric stenosis (IHPS) is a relatively common disease that primarily affects young infants. The underlying stenosis causes functional obstruction of the pyloric canal. Consequently, gastric emptying of milk is disturbed severely. IHPS involves hypertrophy and hyperplasia of the pyloric smooth muscle mass and results in pyloric stenosis (Oue and Puri, *Pediatr. Res.* 45: 853-857 [1999]). Furthermore, increased expression of EGF, EGF receptor and HB-EGF has been reported, in SMCs in pyloric circular and longitudinal muscle from IHPS patients as compared to control tissues (Shima et al., *Pediatr. Res.* 47: 201-207 [2000]). The antagonists of ErbB4 disclosed herein may find use in the control of pyloric smooth muscle cell proliferation and therefore in the treatment of pyloric stenosis.

The contractile nature of smooth muscle cells and regulation of their contraction by various factors play a crucial role in the urinary collecting system including bladder, ureters and urethra. A membrane-bound precursor form of HB-EGF is expressed in urinary bladder smooth muscle cells and epithelial cells (Freeman et al., *J. Clin. Invest.* 99: 1028-1036 [1997]; Kaefer et al., *J. Urol.* 163: 580-584 [2000]). Moreover, treatment of bladder SMCs with diphtheria toxin, which is known to utilize membrane-bound HB-EGF as a receptor, inhibited their proliferation (Kaefer et al., ibid). HB-EGF is a potent mitogen for bladder SMC proliferation, and it acts by binding to ErbB1 (HER1) receptors expressed by these cells, thus acting as an autocrine growth factor (Borer et al., *Lab Invest.* 79: 1335-1345 [1999]). The authors also demonstrated the expression of ErbB2 and ErbB3 but not ErbB4 receptors on bladder SMCs. These findings raise the possibility that HB-EGF plays a role in the bladder wall thickening that occurs in response to obstructive syndromes affecting the lower urinary tract. Therefore, ErbB4 antagonists of the instant invention, particularly ErbB4 immunoadhesin, may prove useful in controlling proliferation of bladder smooth muscle cells, and consequently in the prevention or treatment of urinary obstructive syndromes.

The obstructive airway diseases are yet another group of diseases with underlying pathology involving smooth muscle cell proliferation. One example of this group is asthma which manifests in airway inflammation and bronchoconstriction. EGF has been shown to stimulate proliferation of human airway SMCs and is likely to be one of the factors involved in the pathological proliferation of airway SMCs in obstructive airway diseases (Cerutis et al., *Am. J. Physiol.* 273: L10-15 [1997]; Cohen et al., *Am. J. Respir. Cell. Mol. Biol.* 16: 85-90 [1997]). Accordingly, the ErbB4 antagonists of the present invention may be used for the treatment of obstructive airway diseases.

There are two major approaches to introducing the nucleic acid (optionally contained in a vector) into the patient's cells; in vivo and ex vivo. For in vivo delivery the nucleic acid is injected directly into the patient, usually at the site where the chimeric heteroadhesin is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187).

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc.

A commonly used vector for ex vivo delivery of the gene is a retrovirus. The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al, J. Biol. Chem. 262: 4429-4432 (1987); and Wagner et al, Proc. Natl. Acad. Sci. USA 87:3410-3414 (1990). For review of the currently known gene marking and gene therapy protocols see Anderson et al., Science 256:808-813 (1992). See also WO 93/25673 and the references cited therein.

Therapeutic formulations are prepared for storage by mixing the ErbB4 antagonist having the desired degree of purity with optional physiologically acceptable carriers, excipients, or stabilizers (Remington's Pharmaceutical Sciences, 16th Edition, Osol., A., Ed., (1980)), in the form of lyophilized cake or aqueous solutions. Pharmaceutically acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics, or polyethylene glycol (PEG).

An antibody or an immunoadhesin to be used for in vivo administration must be sterile. This is readily accomplished by filtration through sterile filtration membranes, prior to or following lyophilization and reconstitution. The formulation ordinarily will be stored in lyophilized form or in solution.

Therapeutic compositions are generally placed into a container having a sterile access port, for example, an intravenous solution bag or vial having a stopper pierceable by a hypodermic injection needle.

The route of antibody, immunoadhesin or chimeric heteroadhesin administration is in accord with known methods, e.g., injection or infusion by intravenous, intraperitoneal, intracerebral, intramuscular, intraocular, intraarterial, or intralesional routes, or by sustained-release systems as noted below. The heteroadhesin or antibody is administered continuously by infusion or by bolus injection.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., J. Biomed. Mater. Res., 15:167-277 (1981) and Langer, Chem. Tech., 12:98-105 (1982) or poly(vinylalcohol)), polylactides (U.S. Pat. No. 3,773,919, EP 58,481), copolymers of L-glutamic acid and gamma ethyl-L-glutamate (Sidman et al., Biopolymers, 22:547-556 (1983)), non-degradable ethylene-vinyl acetate (Langer et al., supra), degradable lactic acid-glycolic acid copolymers such as the Lupron Depot (injectable microspheres composed of lactic acid-glycolic acid copolymer and leuprolide acetate), and poly-D-(–)-3-hydroxybutyric acid (EP 133,988).

Sustained-release ErbB4 antagonist also include liposomally entrapped drug. Liposomes containing ErbB4 antagonist are prepared by methods known per se: Epstein at al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal therapy. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent (such as Doxorubicin) is optionally contained within the liposome. See Gabizon et al. J. National Cancer Inst. 81(19):1484 (1989).

The ErbB4 antagonist of the invention may be used to bind and sequester ErbB4 ligand or block ErbB4 receptor thereby inhibiting ErbB4 activation in the cell and inhibit cell proliferation. The ErbB4 antagonist of the invention may be administered to a patient along with other therapy such as a chemotherapeutic agent. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the antagonist or may be given simultaneously therewith.

An effective amount of antagonist to be employed therapeutically will depend, for example, upon the therapeutic objectives, the route of administration, and the condition of the patient. Accordingly, it will be necessary for the therapist to titer the dosage and modify the route of administration as required to obtain the maximum therapeutic effect. A typical dosage might range from about 1 g/kg to up to 100 mg/kg of patient body weight, preferably about 10 g/kg to 10 mg/kg. Typically, the clinician will administer antagonist until a dosage is reached that achieves the desired effect for treatment of the above mentioned disorders.

5. Methods for Identification of Molecules that Inhibit or Enhance the Proliferation or Migration of Smooth Muscle Cells The present invention discloses a method of screening to identify molecules that can inhibit or enhance the proliferation of smooth muscle cells. For example, a candidate molecule is incubated with a polypeptide comprising the extracellular domain of an ErbB4 receptor, followed by adding to a culture of smooth muscle cells and determining the effect on the proliferation of cells. The ErbB4 receptor may be a native ErbB4 receptor such as a human ErbB4 receptor, or may be a polypeptide having at least 85% sequence identity with the amino acid sequence of a native ErbB4 receptor. The cell proliferation can be monitored and quantitated in a number of ways. For instance, incorporation of $^3$H-thymidine into DNA is a well-established method to monitor cellular DNA synthesis indicative of cell proliferation. The incorporation of $^3$H-thymidine into DNA is monitored either microscopically by counting the number of silver grains in an autoradiograph or biochemically by liquid scintillation counting. Similarly, incorporation of 5-bromo 2'-deoxyuridine (BrdU) into cellular DNA can be monitored either microscopically or immunologically. Both assays utilize highly specific monoclonal antibodies that recognize BrdU incorporated into DNA. In the microscopic assay, the cells are permeabilized, reacted with BrdU specific monoclonal antibodies followed by labeled secondary antibodies. The secondary antibodies are detected by virtue of an attached label such as a fluorescent dye (fluorescein isothiocyanate (FITC), rhodamine, Texas Red etc) or an enzymatic label (alkaline phosphatase, horseradish peroxidase etc). A suitable substrate that produces an insoluble product upon enzymatic action is then used to reveal and quantitate the enzyme labeled secondary antibodies. An enzymatic assay monitors the amount of BrdU specific monoclonal antibodies by a suitable immunoassay such as ELISA. The monoclonal antibodies specific for BrdU as well as ELISA kits containing such antibodies are available commercially from a number of sources including Boehringer Mannheim. A flow cytometry can also be used to monitor cell proliferation. In this method, cells are fractionated based on the nuclear DNA content per cell. Since the nuclear DNA content varies among cells undergoing division depending on the phase of cell cycle (2n in G1 phase, 4n in G2+M phase and intermediate value in S phase, wherein n is the value of haploid nuclear DNA content), cell proliferation can be rapidly monitored by estimating the fraction of cells in S and G2+M phases using this approach.

Since ErbB4-dependent proliferation of smooth, muscle cells involves ligand-mediated signal transduction pathway utilizing ErbB4 receptor, any step in this pathway can be monitored and used as a measure of cell proliferation. One such step is a ligand-induced tyrosine autophosphorylation of ErbB4 receptor, which can be monitored by the kinase receptor activation (KIRA) assay as described in WO95/14930. This ELISA-type assay is suitable for qualitative or quantitative measurement of kinase activation by measuring the autophosphorylation of the kinase domain of a receptor protein tyrosine kinase such as ErbB4. The first stage of the assay involves phosphorylation of the kinase domain of ErbB4 receptor present in the cell membrane of a smooth muscle cell. Typically, a first solid phase (e.g., a well of a first assay plate) is coated with a substantially homogeneous population of smooth muscle cells. Being adherent cells, the smooth muscle cells adhere naturally to the first solid phase. One can also use smooth muscle cells transfected with a "receptor construct" that comprises a fusion of a kinase receptor and a flag polypeptide. Antibodies specific for flag polypeptide are used in the ELISA part of the assay to capture the receptor with flag peptide. A candidate molecule and a polypeptide comprising the extracellular domain of a native ErbB4 receptor are then added to the wells containing smooth muscle cells, followed by monitoring tyrosine autophosphorylation of ErbB4 receptor by the KIRA assay. A polypeptide comprising an amino acid sequence having at least 85% sequence identity with the amino acid sequence of the extracellular domain of ErbB4 receptor can also be used in the assay. Following exposure, the smooth muscle cells are solubilized using a lysis buffer (which has a solubilizing detergent therein) and gentle agitation, thereby releasing cell lysate which can be subjected to the ELISA part of the assay directly, without the need for concentration or clarification of the cell lysate.

The cell lysate thus prepared is then subjected to the second (ELISA) stage of the assay. As a first step in the ELISA stage, a second solid phase (usually a well of an ELISA microtiter plate) is coated with a capture agent (often a capture antibody) which binds specifically to ErbB4 receptor or, in the case of a receptor construct, to the flag polypeptide. Coating of the second solid phase is carried out so that the capture agent adheres to the second solid phase. The capture agent is generally a monoclonal antibody but polyclonal antibodies may also be used. The cell lysate obtained is then exposed to, or contacted with, the adhering capture agent so that the receptor or receptor construct adheres to (or is captured in) the second solid phase. A washing step is then carried out, so as to remove unbound cell lysate, leaving the captured receptor or receptor construct. The adhering or captured receptor or receptor construct is then exposed to, or contacted with, an anti-phosphotyrosine antibody which identifies phosphorylated tyrosine residues in the tyrosine kinase receptor. In the preferred embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule. Finally, binding of the anti-phosphotyrosine antibody to the captured receptor or receptor construct is measured, e.g., by a color change in the color reagent. Anti-phosphotyrosine antibodies that are commercially available can be used for the assay.

The instant invention also provides for a method for screening of molecules which can inhibit or enhance migration of smooth muscle cells. One of the formats utilizes a compartmentalized chemotaxis cell culture chambers such as Neuroprobe ChemoTX chemotaxis chambers available from (Neuroprobe Inc., Gaithersburg, Md.). In this method, a porous filter separates smooth muscle cells in the upper chamber from a medium containing a chemoattractant (e.g. thrombin) in the lower chamber. Smooth muscle cells are incubated with a candidate molecule and a polypeptide comprising the extracellular domain of an ErbB4 receptor. At the end of incubation period, the filters are stained and smooth muscle cells that have migrated to the bottom of the filter are counted using an inverted microscope.

A conventional library or a combinatorial library of chemical compounds can be used for screening purpose. An automated approach adapted for high throughput can be conveniently used for the assay. However, the screening assays are not restricted only to small molecules, even macromolecules such as antibodies can be used for the screening.

EXAMPLES

The following examples are offered by way of illustration and not by way of limitation. The examples are provided so as to provide those of ordinary skill in the art with a complete disclosure and description of how to make and use the compounds, compositions, and methods of the invention and are not intended to limit the scope of what the inventors regard as their invention. Efforts have been made to insure accuracy with respect to numbers used (e.g. amounts, temperature, etc.) but some experimental errors and deviation should be accounted for. Unless indicated otherwise, parts are parts by weight, temperature is in degrees C., and pressure is at or near atmospheric. The disclosures of all citations in the specification are expressly incorporated herein by reference.

Example 1

Construction, Isolation and Biochemical Characterization of Immunoadhesins and Chimeric Heteromultimer Immunoadhesins A unique Mlu I site was engineered into a plasmid expressing human IgG heavy chain (pDR, a gift from J. Ridgeway and P. Carter, Genentech, Inc.) at the region encoding the hinge domain of the immunoglobulin. Mlu I sites were also engineered into a set of ErbB4 expression plasmids at the region encoding the ECD/TM junctions of these receptors. All mutagenesis were performed using the Kunkel method (Kunkel, T., Proc. Natl. Acad. Sci. U.S.A. 82:488 (1985)). The Mlu I sites were utilized to make the appropriate ErbB4-IgG fusion constructs. The fusion junction of the ErbB-IgG chimera was: $G^{640}{}_{ErbB4}$-(TR)-$DKTH^{224}{}_{VH}$, where the amino acid numbering of the ErbB4 polypeptide is describe in Plowman et al. (Plowman, G. D. et al., (1993a) PNAS USA 90:1746-1750) The conserved TR sequence is derived from the Mlu I site. The sequence of the Fc region used in the preparation of the fusion constructs is found in Ellison, J. W. et al (Ellison, J. W. et al. (1982) NAR 10:4071-4079). The final expression constructs were in a pRK-type plasmid backbone wherein eukaryotic expression is driven by a CMV promoter (Gorman et al., DNA Prot. Eng. Tech. 2:3-10 (1990)).

To obtain protein for in vitro experiments, adherent HEK-293 cells (ATCC No. CRL-1573) were transfected with the expression plasmid using standard calcium phosphate methods (Gorman et al., supra and Huang at al., Nucleic Acids Res. 18:937-947 (1990)). Serum-containing media was replaced with serum-free media 15 hours post-transfection and the transfected cells incubated for 5-7 days. The resulting conditioned media was harvested and passed through Protein A columns (1 ml Pharmacia HiTrap). Purified IgG fusions were eluted with 0.1 M citric acid (pH 4.2) into tubes containing 1 M Tris pH 9.0. The eluted proteins were subsequently dialyzed against PBS and concentrated using Centri-prep-30 filters (Amicon). Glycerol was added to a final concentration of 25% and the material stored at −20 C. Concentrations of material were determined via a Fc-ELISA $^{125}$I-HRG Binding Assay The EGF-like domain of HRG $1_{(177-244)}$ was expressed in E. coli, purified and radioiodinated as described previously (Sliwkowski, M. et al. J. Biol. Chem. 269:14661-14665 (1994)). Full-length rHRG 1, which was expressed in Chinese hamster ovary cells, was used in Western blot analysis. Binding assays were performed in Nunc breakapart immuno-module plates. Plate wells were coated at 4 C overnight with 100 l of 5 g/ml goat-anti-human antibody (Boehringer Mannheim) in 50 mM carbonate buffer (pH 9.6). Plates were rinsed twice with 200 l wash buffer (PBS/0.05% Tween-20) followed by a brief incubation with 100 l 1% BSA/PBS for 30 min at room temperature. Buffer was removed and each well was incubated with 100 l IgG fusion protein in 1% BSA/PBS under vigorous side-to-side rotation for 1 hour. Plates were rinsed three times with wash buffer and competitive binding was carried out by adding various amounts of cold competitor -HRG and $^{125}$I-HRG 1 and incubating at room temperature for 2-3 hours with vigorous side-to-side rotation. Wells were quickly rinsed three times with wash buffer, drained and individual wells were counted using a 100 Series Iso Data-counter. Scatchard analysis was performed using a modified Ligand program (Munson, P. and Robard, D. (1980) Analytical Biochemistry 107:220-239).

$^{3}$H-Thymidine Incorporation Assay

Tritiated thymidine incorporation assays were performed in a 96-well format. MCF7 cells were plated at 10,000 cells/well in 50:50 F12/DMEM (high glucose) 0.1% fetal calf serum (100 ml). Cells were allowed to settle for 3 hours, after which ErbB4-IgG fusion proteins and/or heregulin were added to the wells (final volume of 200 ml) and the plates incubated for 15 hours in a 37° C. tissue culture incubator. Tritiated thymidine was added to the wells (20 ml of 1120 diluted tritiated thymidine stock: Amersham TRA 120 B363, 1 mCi/ml) and the plates incubated a further 3 hours. Tritiated material was then harvested onto GF/C unifilters (96 well format) using a Packard Filtermate 196 harvester. Filters were counted using a Packard Topcount apparatus.

Example 2

Effect of ErbB4-IgG Immunoadhesin on Human Aortic Smooth Muscle Cell Proliferation Human aortic smooth muscle cells (Clonetics) were seeded at about 50% confluent density (5000 cells/well) in 96 well tissue culture plates and incubated overnight in SM2 media (Clonetics). Next day, the media was changed to M199 supplemented with ITS (1×), 2 mM L-glutamine, 50 µg/ml ascorbic acid, 26.5 mM NaHCO3, 100 U/ml penicillin, 100 U/ml streptomycin and 0.1% (v/v) fetal bovine serum. The cells were further incubated for 16 h. The cells were then treated with either Her4-IgG (400 nM) or buffer for 1 h, followed by treatment with PDGF (100 ng/ml) for 40 h. Control cells were left untreated to estimate the basal level of cell growth. An aliquot of BrdU (10 µl/well of a 10 µM solution of 5-bromo 2'-deoxyuridine prepared in PBS) was added and the cells were incubated for an additional 2 h. Cell proliferation was monitored by quantitating BrdU incorporation using BrdU ELISA (Cell proliferation kit, Boehringer mannheim, Catalog No 1 647 229) following manufacturer's instructions for adherent cells.

As shown in FIG. 5, PDGF stimulated growth of aortic smooth muscle cells in agreement with earlier reports (Ross et al., Philos. Trans. R. Soc. Lond. B Biol. Sci. 12: 155-169 [1990]). Pre-treatment of cells with ErbB4-IgG immunoadhesin reduced the extent of PDGF-stimulated proliferation of cells. Control cells treated with buffer in place of ErbB4-IgG did not show any significant effect on cell proliferation. These data indicate that at least part of the mitotic response of smooth muscle cells is mediated by the activation of the ErbB4 receptor, and removal of ligands which would activate the ErbB4 receptor with the ErbB4 immunoadhesin reduces smooth muscle cell proliferation in response to PDGF.

Example 3

Effect of ErbB4-IgG Immunoadhesin on Human Aortic Smooth Muscle Cell Migration Human aortic smooth muscle cells were trypsinized and resuspended at a concentration of $5 \times 10^5$ cells per ml in DME containing 10% FBS. Cells were preincubated with Her4-IgG (400 nM) or buffer for 15 min. The lower wells of ChemoTX chemotaxis chambers (Neuroprobe Inc., Cat 116-8) were filled with 300 µl of a solution of 2 U/ml human thrombin or buffer (PBS) negative control. A filter was mounted on top of the chamber and the smooth muscle cells (buffer or ErbB4 treated) were added to the top wells in a volume of 50 µl. The plate and filter were covered with the clear plastic lid and incubated for 3 h at 37° C. in humidified air with 5% $CO_2$. At the end of the incubation filters were removed and the top sides were wiped with a Q-tip to remove any remaining cells. The filters were stained with Dif-Quick staining solution and the number of cells migrated to the bottom of the filter were counted using an inverted phase microscope. Six wells in each group and 40 fields in each well were counted.

Figure 6:
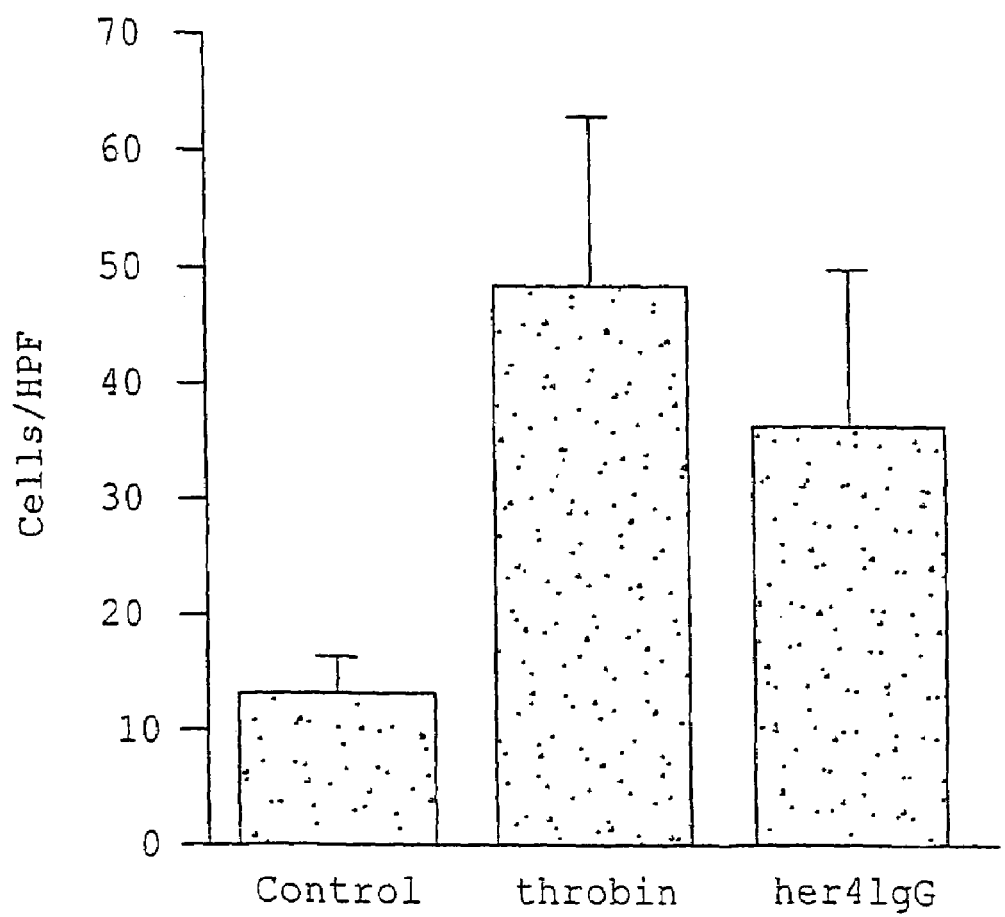
FIG. 6 shows the effect of ErbB4-IgG immunoadhesin on the chemotactic response of human aortic smooth muscle cells to thrombin.

As shown in FIG. 6, thrombin acted as a chemotactic stimulus and induced migration of aortic smooth muscle cells. ErbB4-IgG immunoadhesin inhibited thrombin-stimulated cell migration. These data indicate that at least part of thrombin's ability to stimulate smooth muscle cell migration is mediated by the release of ligand(s) for the ErbB4 receptor, and that the removal of these ligands with the ErbB4 immunoadhesin reduces the chemotactic response to thrombin

Example 4

Production and Characterization of Anti-ErbB4 Monoclonal Antibodies

Generation of anti-ErbB4 Mabs

A panel of 34 murine monoclonal antibodies which specifically bind the extracellular domain of ErbB4 were produced using conventional hybridoma technology (Table 2). Total cellular RNA was extracted from MDA-MB-453 cells and used as a template in RT PCR to generate the human ErbB4 extracellular domain (ECD) coding sequence. Specific oligonucleotides used in the RT PCR reactions were synthesized on the basis of the ErbB4 DNA sequence. A gDErbB4 ECD fusion protein was constructed by ligating the coding sequences for amino acids 1-52 of herpes simplex virus type 1 glycoprotein D to the sequences encoding amino acids 26-640 of human ErbB4. The gDErbB4 ECD cDNA was inserted into the cytomegalovirus-based expression vector pRK5. This construct was transiently transfected into human embryonic kidney 293 cells using a standard calcium phosphate precipitation protocol.

An affinity column was prepared by coupling the anti-gD monoclonal 5B6 to CNBR sepharose (Pharmacia LKB Biotechnology, Uppsala Sweden). Supernatant from gDErbB4 ECD transfected 293 cells was concentrated 20-40 fold on a ym30 membrane (Amicon, Beverly Mass.) and loaded onto the affinity resin. The column was washed with PBS and the receptor was eluted with 100 mM acetic acid 500 mM NaCl pH 2.4. The ErbB4 ECD was buffer exchanged into PBS and concentrated. Protein concentration was determined by OD280.

Balb/c mice were immunized with approximately 5 g of ErbB4 ECD in RIBI MPL+TDM+CWS Emulsion (RIBI ImmunoChem Research Inc., Hamilton, Mont.) in their rear footpads on weeks 0, 1, 2 and 3. The immunized mice were tested for an antibody response by ELISA. The mice with the highest titers were given an additional 5 g of ErbB4 ECD in RIBI during week 4. Three days later, the lymphocytes from the popliteal and inguinal nodes were fused with mouse myeloma line X63-Ag8.653. Fused cells were plated at a density of 200,000 cells per well in 96-well tissue culture plates and hybridoma selection using HAT media supplement (Sigma, St. Louis, Mo.) began one day post fusion. Beginning on day 10, the hybridoma supernatants were screened for the presence of ErbB4 specific antibodies using a radioactive capture assay as described below. Stable antibody producing clones were obtained by limiting dilution and large quantities of specific Mabs were produced in ascites. The antibodies were purified on protein A-Sepharose columns (Fermentech, Inc., Edinburgh, Scotland) and stored sterile in PBS at 4° C.

In the radioactive capture assay, Maxisorp breakapart modules (Nunc, Roskilde, Denmark) were coated with 100 l of 2 g/ml goat anti-mouse IgG (Boehringer Mannheim) overnight at 4 C. The plates were washed with PBS/0.5% Tween 20 (PBST), blocked with ELISA diluent (PBS/0.5% BSA/0.05% Tween 20) and incubated with monoclonal supernatants for 2 hr at ambient temperature. The plates were washed and incubated for an additional hour with 40,000 counts/well of $[^{125}I]$ErbB4 ECD. After washing, the amount of ErbB4 bound to the antibodies was determined by counting the wells on a Wallac 1277 GammaMaster (Wallac Inc, Gaithersburg, Md.).

The 34 anti-ErbB4 monoclonal antibodies produced by this method (Table 2) have a high affinity for the receptor, exhibit a diversity of isotypes and are directed to 18 distinct epitopes on the ErbB4 ECD. Isotypes of the antibodies were determined using a Mouse MonoAb ID/SP isotyping kit from Zymed (So. San Francisco, Calif.), following supplier's instructions.

Testing the Specificity of Anti-ErbB4 Antibodies

The specificity of the Mabs was determined in an ELISA measuring their ability to bind immobilized HER2, HER3 and ErbB4 extracellular domains (amino acids 1-645, 1-617 and 1-640 respectively). ECDs were coated on ELISA plates at a concentration of 1 g/ml and incubated with biotinylated anti-ErbB4 Mabs. Bound Mabs were detected using streptavidin peroxidase (Sigma, St. Louis, Mo.) and the substrate OPD (Sigma, St. Louis, Mo.). As can be seen in Table 2, nearly all of the antibodies produced were highly specific for ErbB4 (indicated by a '4' in the column labeled 'Specificity'). Four of the antibodies showed some binding to HER3 (indicated by a '3' in the column labeled 'Specificity').

Epitope Mapping and Characterization

The ErbB4 epitope bound by each of the monoclonal antibodies was determined by competitive binding analysis (Fendly et al. *Cancer Research* 50:1550-1558 (1990)). The anti-ErbB4 Mabs were diluted to a concentration of 25 g/ml in ELISA diluent and 50 l was added to an ELISA plate precoated with gDErbB4 ECD as above. The plates were incubated at room temperature for 2 hours and washed with PBST. Dilutions of biotinylated anti-ErbB4 antibodies ranging from 1:1,000 to 1:10,000 were prepared and 50 l was added to the assay plate. Following a one-hour room temperature incubation, the plates were washed and 50 l of a 1:5000 dilution of streptavidin peroxidase (Sigma) was added. The plates were developed using OPD (Sigma). The anti-ErbB4 Mabs were grouped into epitopes based on their ability to block binding of the others by 50% or greater in comparison to an irrelevant Mab control. The relative epitope mapping identified 17 distinct epitopes, identified in Table 2 as A-Q.

The activities of nine representative antibodies were investigated further.

TABLE 2

Summary table of anti-ErbB4 monoclonals

| Mab | Isotype | Epitope | Specificity |
|---|---|---|---|
| 4-1440 | IgG2b, κ | B | 4 |
| 4-1441 | IgG1, κ | J | 4 |
| 4-1459 | IgG2a, κ | D | 4 |
| 4-1460 | IgG1, κ | C | 4 |
| 4-1461 | IgG2a, κ | E | 4 |
| 4-1462 | IgG1, κ | C | 4 |
| 4-1463 | IgG2a, κ | D | 4 |
| 4-1464 | IgG2b, κ | C | 4 |
| 4-1465 | IgG2a, κ | L | 3, 4 |
| 4-1472 | IgG2a, κ | M | 4 |
| 4-1473 | IgG2a, κ | F | 4 |
| 4-1474 | IgG2b, κ | G | 4 |
| 4-1475 | IgG2b, κ | P | 4 |
| 4-1476 | IgG2a, κ | K | 4 |
| 4-1477 | IgG2a, κ | Q | 4 |
| 4-1478 | IgG2a, κ | I | 4 |
| 4-1479 | IgG2a, κ | D | 4 |
| 4-1481 | IgG2a, κ | H | 3, 4 |
| 4-1482 | IgG2b, κ | H | 4 |
| 4-1483 | IgG1, κ | R | 3, 4 |
| 4-1484 | IgG1, κ | E | 4 |
| 4-1485 | IgG2a, κ | F | 4 |
| 4-1491 | IgG2a, κ | G | 4 |
| 4-1492 | IgG2b, κ | A | 4 |
| 4-1493 | IgG2B, κ | A | 4 |
| 4-1494 | IgG2b, κ | B | 4 |
| 4-1495 | IgG2b, κ | A | 4 |
| 4-1496 | IgG1, κ | A | 3, 4 |
| 4-1497 | IgG1, κ | N | 4 |
| 4-1498 | IgG2b, κ | E | 4 |
| 4-1535 | IgG2b, κ | B | 4 |
| 4-1536 | IgG2b, κ | A | 4 |
| 4-1537 | IgG2b, κ | B | 4 |
| 4-1543 | IgG2a, κ | O | 4 |

Determination of Binding Affinity

The relative affinities of the anti-ErbB4 Mabs were determined according to the method described by Friguet et al. (J Immunol Methods. 77(2):305-19 (1985)). Various concentrations of the ErbB4 ECD ($1.1 \times 10^{-7}$ M to $1.08 \times 10^{-10}$ M) were mixed with a constant concentration of anti-ErbB4 Mab ($2.08 \times 10^{-10}$ M) and incubated overnight at 4° C. Following incubation, the unbound Mabs were assayed by adding 100 l of the reaction mixture in duplicate to microtiter plates (Nunc) previously coated with gDErbB4 ECD (100 l/well at a concentration of 1 g/ml in 0.05M carbonate buffer, pH 9.6 for 16 hr at 4° C.) and incubated for 1 hour at room temperature. After washing with PBST the bound Mabs were detected by adding 100 l/well of a 1:5000 dilution of goat anti-mouse F(ab')$_2$ peroxidase (Boehringer Mannheim) for one hour at room temperature. The plates were developed using o-phenylenediamine dihydrochloride substrate (OPD, Sigma, St. Louis, Mo.) and read on a platereader.

The Mabs all showed high affinity binding, with Kd's ranging from 0.4 to 12 nm as presented in Table 3.

Non-Reducing Immunoblot

The ability of the anti-ErbB4 Mabs to bind reduced and nonreduced ErbB4 ECD was tested by immunoblot analysis. ErbB4 ECD was added to tricine sample buffer, with and without BME, and applied to a 10-20% Novex tricine gel (Novex, San Diego, Calif.). The gel was run at 100V and electroblotted for 60 min. at 0.5 amp onto a PVDF, Immobilon P, membrane (Millipore, Bedford Mass.). The membrane was washed with PBST and blocked overnight with PBS/0.5% BSA/0.1% Tween 20, and incubated with 1 g/ml monoclonal antibody for 1.5 hour at ambient temperature. The membrane was washed and incubated for an additional hour with a 1:10,000 dilution of rat anti-mouse IgG peroxidase (Boehringer Mannheim). The membrane was washed thoroughly and developed using the Amersham ECL chemiluminescence system (Amersham Life Science Inc., Arlington Heights, Ill.).

None of the Mabs were able to recognize reduced ErbB4 ECD (data not shown), suggesting that they are directed to conformational epitopes. Mabs identified as positive in Table 3 are those that are able to recognize low concentrations of non-reduced ErbB4 ECD. Mabs 4-1459, 4-1460, 4-1461, 4-1462, 4-1492 and 4-1497 demonstrated a high level of immunoreactivity and were able to bind non-reduced ErbB4 ECD at levels down to 0.3 ng.

Inhibition of HRG Binding

A K562 cell line that does not express any EGFR-like receptors was used to further characterize the anti ErbB4 monoclonal antibodies. A K562 cell line transfected with ErbB4 (1E10.1H4) was produced and cultured in RPMI 1640 with 2 mM L-glutamine (GIBCO/BRL), 10% FBS (Hyclone) and 800 g/ml Geneticin, G418 (Gibco/BRL). At least 20 hr prior to assay, 1E10.1H4 was stimulated with 10 nm phorbol-12-myristate, 13-acetate (PMA, Calbiochem, La Jolla Calif.). The anti-ErbB4 Mabs were evaluated for their ability to block the binding of HRG to this cell line.

Quadruplicate samples containing $1.0 \times 10^5$ K562 ErbB4 cells resuspended in 200 l of RPMI 1640 with 10 mM HEPES and 0.1% BSA (binding buffer) were incubated with 132 pM [$^{125}$I]HRG $1_{(177-244)}$, in the presence of 100 nM anti-ErbB4 Mabs, overnight on ice. Following incubation, the cells were collected using a Multiscreen filtration device (Millipore), and washed twice with 200 l ice cold binding buffer. Cell associated counts were measured on a gamma counter. The percent binding was calculated against a control sample containing no Mab. The nonspecific binding was determined by incubation of a sample in the presence of 500 nM cold HRG $1_{(177-244)}$. Mabs were considered positive for HRG blocking if they blocked 90% or greater binding. As can be seen in Table 3, six of the nine anti-ErbB4 antibodies tested were able to inhibit $^{125}$I-HRG binding at this level. Mab 4-1461 inhibited bindin by 7% and 1459 exhibited no HRG blocking. The anti-ErbB4 Mab 4-1497 did not inhibit binding but rather appeared to enhance HRG binding by 26%.

Inhibition of HRG Binding in Human Breast Cancer Cell Lines

Since a number of the anti-ErbB4 Mabs were able to block binding of HRG to transfected K562 cells, their ability to block HRG binding to several human mammary carcinoma cell lines was tested. The cell lines MDA-MB-453, T47D and BT474 (ATCC, Rockville, Md.) were plated into 24 well tissue culture plates at a density of $1 \times 10^5$ cells per well and allowed to adhere overnight. The anti-ErbB4 Mabs or anti-HER-2 control Mabs 2C4 and 4D5 were diluted to a concentration of 100 nM in Ham's F-12 plus Dulbecco's modified Eagle medium (1:1, v/v) with 10 mM HEPES and 0.1% BSA (binding buffer) and added in triplicate to the plates. Following a 30 minute incubation on ice, $1.5 \times 10^5$ counts of [$^{125}$I] HRG $1_{(144-277)}$ was added. The plates were incubated on ice for four hours and washed twice with ice cold binding buffer. The cells were solubilized with 8 M urea/3 M acetic acid and cell associated counts were measured on a Wallac 1277 GammaMaster. The percent binding was calculated as above. The nonspecific binding was determined by incubation of a sample in the presence of 100 nM cold HRG $1_{(144-277)}$.

None of the anti-ErbB4 Mabs caused significant inhibition of $^{125}$IHRG binding to the carcinoma lines tested. In contrast, the anti-HER-2 control Mabs 2C4 and 4D5 blocked binding by 84% and 29% respectively in MDA-MB-453 cells, 70% and 48% in T47D cells and 57% and 12% in BT474 cells. The unlabeled HRG control blocked 99% binding in MDA-MB 453 cells, 98% binding in T47D cells and 96% binding in BT474 cells at a concentration of 100 nM. This data suggests that in these cell lines the ErbB4 receptor may play a minor role in mediating the HRG responses.

Inhibition of Tyrosine Phosphorylation

Hereulins have been shown to induce the tyrosine phosphorylation of ErbB4. Therefore it was of interest to determine if the anti-ErbB4 Mabs were able to affect HRGβ$1_{(177,244)}$ stimulated phosphorylation of the receptor in the K562 ErbB4 cell line.

The ErbB4 transfected K562 cell line (1E10.1H4) was grown in RPMI 1640 culture media to a density of $1 \times 10^6$ cells/ml. The cells were then changed to serum-free media without PMA (assay buffer) and incubated at 37° C. for 2-6 hours. The cells were washed with assay buffer and duplicate samples containing $2.5 \times 10^5$ cells in assay buffer with 0.1% BSA, were incubated with 25 ug of anti-ErbB4 Mabs or a control Mab for 30 min. at room temperature. Following incubation, one set of the samples was stimulated with 15 mM HRG $1_{(177-244)}$ for 8 minutes at room temperature. The supernatants were removed and the cells lysed for 5 minutes at 100° C. in 100 1 of SDS sample buffer containing 50 l/ml-mercaptoethanol. A 30 1 aliquot of each sample was electrophoresed in a 4-12% polyacrylamide gel (Novex) and electroblotted onto a PVDF membrane (Millipore). The membranes were blocked with 2% BSA in tris-buffered saline containing 0.05% Tween-20 overnight at 4° C. and incubated with a 1:1000 dilution of recombinant antiphosphotyrosine peroxidase monoclonal RC20H (Transduction Laboratories, Lexington Ky.) for 4 hours at room temperature. Bound anti-phosphotyrosine Ab was visualized using the Amersham ECL system (Amersham Life Science Inc.) and quantified by densitometry.

Six of nine monoclonal antibodies tested inhibited the generation of an HRG-induced tyrosine phosphorylation signal (Table 31. The remaining three were not inhibitory and none of the anti-ErbB4 Mabs was able to stimulate phosphorylation of the ErbB4 receptor.

Immunohistochemistry

Since anti-ErbB4 Mabs may be useful as diagnostic reagents, their ability to stain frozen cell pellets using standard immunocytochemical techniques was investigated. ErbB4 transfected K562 cells (1E10.1H4) and the human breast carcinoma lines MDA-MB-453, T470, and BT474 (ATCC, Rockville, Md.) were pelleted and frozen in OCT compound (Miles Inc., Elkhart, Ind.). The frozen pellets were sectioned on a cryostat to a thickness of 5 microns, mounted on slides, fixed in cold acetone (4 C) for 3-5 min. and air-dried. Endogenous peroxidase activity was quenched using a modification of the glucose oxidase method. The slides were rinsed with PBS and the cells were blocked for endogenous biotin activity using a Vector Biotin blocking kit (Vector, Burlingame, Calif.). Endogenous immunoglobulin binding sites were blocked with 10% normal horse serum (Vector). The cells were then incubated with 10 g/ml anti-ErbB4 Mabs for one hour at RT, followed by a 30 minute incubation with a 1:200 dilution of biotinylated horse anti-mouse IgG (Vector). The slides were incubated with ABC Elite Reagent (Vector) for 30 min. and the ErbB4 receptors visualized using DAB (Pierce, Rockford, Ill.). Mayer's hematoxylin (Rowley Biomedical Institute, Rowley, Mass.) was used to counterstain the cells.

Many of the anti-ErbB4 Mabs were able to stain the ErbB4 transfected K562 cells with varying intensity and little or no background staining (Table 3). Numbers represent the intensity of staining compared to an irrelevant control. None of the Mabs was able to stain the frozen human mammary carcinoma cells that were tested (data not shown).

TABLE 3

Summary table of monoclonal antibody activity

| Mab | Isotype | Epitope | Kd(nM) | Non-Reducing Immunoblot | HRG Blocking | P-Tyr Blocking | Histo-chemistry |
|---|---|---|---|---|---|---|---|
| 4-1440 | IgG2b, κ | B | 1.9 | − | + | + | 3+ |
| 4-1459 | IgG2a, κ | D | 0.7 | + | − | − | 4+ |
| 4-1460 | IgG1, κ | C | 1.2 | + | + | + | 3+ |
| 4-1461 | IgG2a, κ | E | 2.3 | + | − | − | 4+ |
| 4-1462 | IgG1, κ | C | 0.4 | + | + | + | 2+ |
| 4-1464 | IgG2b, κ | C | 1.0 | − | + | + | 2+ |
| 4-1473 | IgG2a, κ | F | 6.0 | − | + | + | 2-3+ |
| 4-1492 | IgG2b, κ | A | 2.1 | + | + | + | − |
| 4-1497 | IgG1, κ | N | 12.0 | + | − | − | − |

FACS Analysis

To determine whether the anti-ErbB4 Mabs could bind to ErbB4 on the surface of viable cells, FACS analysis was done using the ErbB4 transfected K562 cell line and the mammary carcinoma lines MDA-MB-453, T47D and BT-474. Adherent cells were detached from tissue culture flasks using 10 mM EDTA in PBS, centrifuged at 1400 rpm for 5 min. and resuspended in PBS with 1% fetal bovine serum (FACS diluent). The cells were counted, adjusted to $10^7$ cells/ml and 0.1 ml of cells was incubated with 10 g/ml of each Mab in 100 l FACS diluent for 30 min. at 4° C. The samples were washed, resuspended in 0.1 ml diluent and incubated with 1 g of FITC conjugated F(ab')$_2$ fragment of goat anti-mouse IgG (Boehringer Mannheim) for 30 min at 4° C. The cells were washed, resuspended in 0.5 ml FACS diluent and analyzed using a FACScan cell sorter (Becton Dickinson, Mt. View, Calif.). Data was gated by forward and side scatter and propidium iodide fluorescence to exclude debris, doublets and dead cells.

All of the Mabs bound to the ErbB4 receptor on the ErbB4 transfected K562 cell line, which is expressed at approximately 2×10⁵ receptors/cell. An increase in observed cellular fluorescence of the ErbB4 transfected K562 cells from 2 to 50 fold was observed when compared to the isotype controls. Some of the weaker binding may reflect a ErbB4 ECD epitope that is sequestered on the intact cells. In contrast, the anti-ErbB4 antibodies 4-1440, 4-1464 and 4-1492, which give the highest fluorescence intensity on the transfected cell line, showed minimal binding to the breast carcinoma lines MDA-MB-453, T47D and BT-474. The positive control anti-HER2 Mab 2-2C4 showed binding to the tumor lines in proportion to the level of HER-2 expression. These results indicate a level of ErbB4 expression on the MDA-MB-453, T470 and BT-474 cells which is below the detection limit of this assay.

Inhibition of Heregulin Binding to ErbB4 Immunoadhesin

Figure 7:
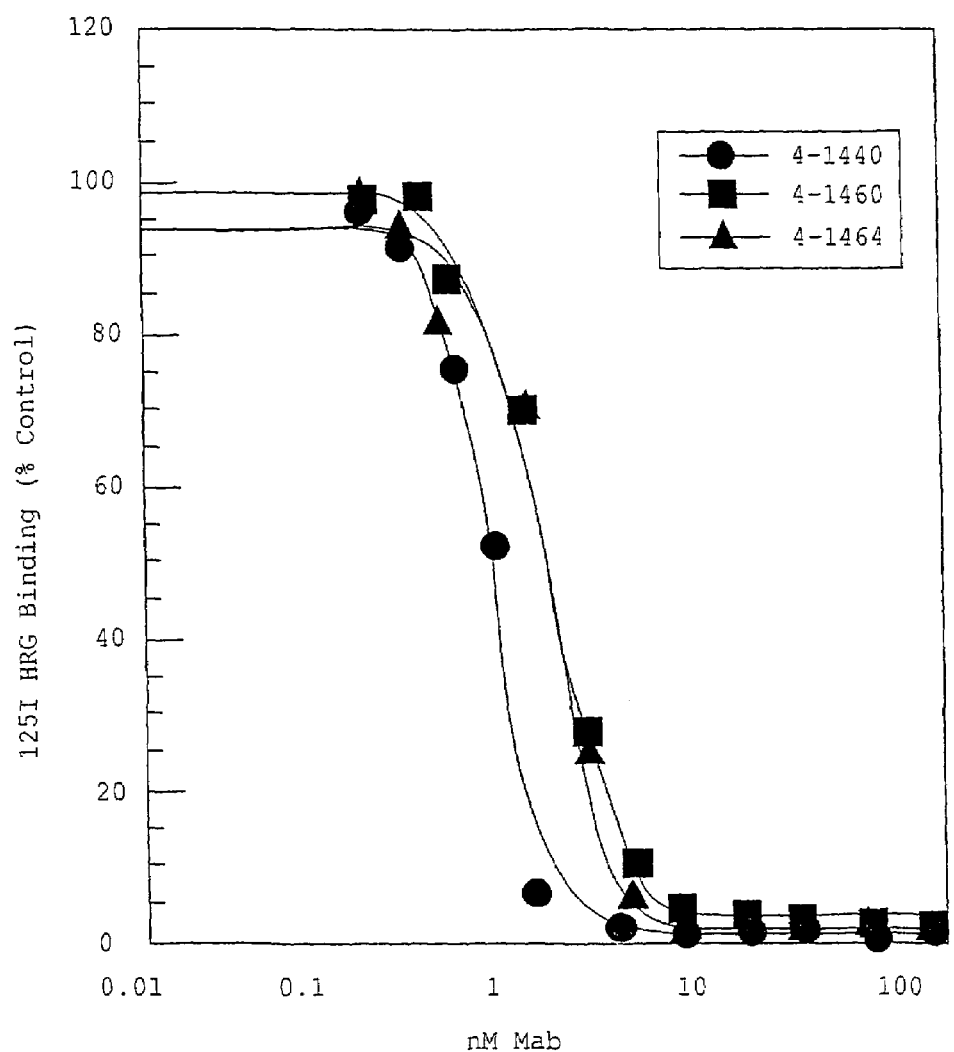
FIG. 7 shows the inhibition of heregulin binding to HER4 immunoadhesin by anti-HER4 monoclonal antibodies.

FIG. 7 shows a displacement curve of $^{125}$IHRG binding to a ErbB4 immunoadhesin captured on breakapart modules using the indicated concentrations of the anti-ErbB4 Mabs 4-1440, 4-1460, and 4-1464. Maxisorp breakapart modules (Nunc) were coated with 100 l of a 1:200 dilution of goat anti-human Ig (Boehringer Mannheim) in 50 mM carbonate buffer pH 9.6 overnight at 4° C. The plates were washed with PBST, blocked with ELISA diluent and incubated with 100 l of 200 ng/ml ErbB4 immunoadhesin for 2 hr at ambient temperature. The plates were washed and 50 l of diluted Mabs (0.1 to 100 nM final) and 50 l of $^{125}$I-HRG $1_{(177-244)}$ diluted to give a final concentration of 132 pM were added to the plate. Following a 1.5 hr incubation at ambient temperature, the plates were washed and the amount of $^{125}$IHRG bound to the receptor was determined by counting the wells on a Wallac 1277 GammaMaster.

FIG. 7 demonstrates that the Mabs inhibited heregulin binding to the immunoadhesin in a dose dependent manner with $ED_{50}$ values ranging from 0.7 to 1.1 nM. This indicates that the Mabs posses a high degree of blocking ability.

Deposit of Material

The following hybridomas have been deposited with the American Type Culture Collection, 10801 University Blvd., Manassas, Va. 20110-2209, USA (ATCC):

| Hybridoma | ATCC Dep. No. | Deposit Date |
| --- | --- | --- |
| HER4.10H1.1A1 | PTA-2828 | Dec. 19, 2000 |
| HER4.1C6.A11 | PTA-2829 | Dec. 19, 2000 |
| HER4.3B9.2C9 | PTA-2826 | Dec. 19, 2000 |
| HER4.1A6.5B3 | PTA-2827 | Dec. 19, 2000 |
| HER4.8B1.2H2 | PTA-2825 | Dec. 19, 2000 |

Each of the deposited hybridomas produces one of the anti-ErbB4 monoclonal antibodies identified in Table 2. HER4.10H1.1A1 produces mAb 4-1464, HER4.1C6.A11 produces mAb 4-1440, HER4.3B9.2C9 produces mAb 4-1460, HER4.1A6.5B3 produces mAb 4-1492 and HER4.8B1.2H2 produces mAb 4-1473

The deposit of the hybridomas with the American Type Culture Collection, Manassas, Va. (ATCC®) was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit and for the longer of a) at least five (5) years after the most recent reguest for the furnishing of a sample of the deposit received by the depository, or b) for the enforceable life of a patent issuing from the present application. The deposit will be made available by ATCC® under the terms of the Budapest Treaty, and subject to an agreement between Genentech, Inc. and ATCC®, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 35 C.F.R. § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated antibody or an antigen binding fragment thereof that specifically binds to human ErbB4 of SEQ ID NO:2 with a Kd less than 100 nM and that comprises all of the complementarity determining regions (CDRs) of a heavy chain and all of the complementarity determining regions (CDRs) of a light chain from an antibody produced by a hybridoma selected from the group consisting of HER4.10H1.1A1 (ATCC Accession number PTA-2828), HER4.1C6.A11 (ATCC Accession Number PTA-2829), HER4.3B9.2C9 (ATCC Accession Number PTA-2826), HER4.1A6.5B3 (ATCC Accession Number PTA-2827) and HER4.8B1.2H2 (ATCC Accession Number PTA-2825), wherein both the heavy chain CDRs and the light chain CDRs are from the same hybridoma.

2. An antibody produced by a hybridoma selected from the group consisting of HER4.10H1.1A1 (ATCC Accession number PTA-2828), HER4.1C6.A11 (ATCC Accession Number PTA-2829), HER4.3B9.2C9 (ATCC Accession Number PTA-2826), HER4.1A6.5B3 (ATCC Accession Number PTA-2827) and HER4.8B1.2H2 (ATCC Accession Number PTA-2825) or an antigen binding fragment thereof.

3. An isolated antibody or an antigen binding fragment thereof that specifically binds to human ErbB4 of SEQ ID NO:2 with a Kd less than 100 nM and that comprises all of the complementarity determining regions (CDRs) from the heavy chain of an antibody selected from the group consisting of anti-ErbB4 monoclonal antibodies 4-1440 produced by HER4.10H1.1A1 (ATCC Accession number PTA-2828), HER4.1C6.A11 (ATCC Accession Number PTA-2829), HER4.3B9.2C9 (ATCC Accession Number PTA-2826), HER4.1A6.5B3 (ATCC Accession Number PTA-2827) and HER4.8B1.2H2 (ATCC Accession Number PTA-2825).

4. An isolated antibody or an antigen binding fragment thereof that specifically binds to human ErbB4 of SEQ ID NO:2 with a Kd less than 100 nM and that comprises all of the complementarity determining regions (CDRs) from the light chain of an antibody selected from the group consisting of anti-ErbB4 monoclonal antibodies 4-1440 produced by HER4.1C6.A11 (ATCC Accession Number PTA-2829), 4-1460 produced by HER4.3B9.2C9 (ATCC Accession Number PTA-2826), 4-1473 produced by HER4.8B1.2H2 (ATCC Accession Number PTA-2825), 4-1492 produced by HER4.1A6.5B3 (ATCC Accession Number PTA-2827), and 4-1464 produced by HER4.10H1.1A1 (ATCC Accession Number PTA-2828).

5. The antibody or binding fragment thereof of claim 1 which specifically binds to ErbB4 with a Kd of less than 50 nM.

6. The antibody or binding fragment thereof of claim 1 which specifically binds to ErbB4 with a Kd of less than 10 nM.

7. The antibody or binding fragment thereof of claim 1 wherein the antibody is a humanized antibody.

8. The antibody or binding fragment thereof of claim 1 wherein the antibody is a human antibody.

9. The antibody or binding fragment thereof of claim 1 which specifically binds to human ErbB4 of SEQ ID NO:2 and which reduces heregulin binding thereto.

10. The antibody or binding fragment thereof of claim 1 which specifically binds to human ErbB4 of SEQ ID NO:2 and which reduces heregulin-induced tyrosine phosphorylation thereof.

11. The antibody or binding fragment thereof of claim 3 which specifically binds to ErbB4 with a Kd of less than 50 nM.

12. The antibody or binding fragment thereof of claim 3 which specifically binds to ErbB4 with a Kd of less than 10 nM.

13. The antibody or binding fragment thereof of claim 3 wherein the antibody is a humanized antibody.

14. The antibody or binding fragment thereof of claim 3 wherein the antibody is a human antibody.

15. The antibody or binding fragment thereof of claim 3 which specifically binds to human ErbB4 of SEQ ID NO:2 and which reduces heregulin binding thereto.

16. The antibody or binding fragment thereof of claim 3 which specifically binds to human ErbB4 of SEQ ID NO:2 and which reduces heregulin-induced tyrosine phosphorylation thereof.

17. The antibody or binding fragment thereof of claim 4 which specifically binds to ErbB4 with a Kd of less than 50 nM.

18. The antibody or binding fragment thereof of claim 4 which specifically binds to ErbB4 with a Kd of less than 10 nM.

19. The antibody or binding fragment thereof of claim 4 wherein the antibody is a humanized antibody.

20. The antibody or binding fragment thereof of claim 4 wherein the antibody is a human antibody.

21. The antibody or binding fragment thereof of claim 4 which specifically binds to human ErbB4 of SEQ ID N0:2 and which reduces heregulin binding thereto.

22. The antibody or binding fragment thereof of claim 4 which specifically binds to human ErbB4 of SEQ ID NO:2 and which reduces heregulin-induced tyrosine phosphorylation thereof.

23. The antibody or binding fragment thereof of claim 2 wherein the antibody binds ErbB4 with a Kd of less than 100 nM.

24. The antibody or binding fragment thereof of claim 23 wherein the antibody binds ErbB4 with a Kd of less than 50 nM.

25. The antibody or binding fragment thereof of claim 24 wherein the antibody binds ErbB4 with a Kd of less than 10 nM.

26. An antibody having the binding specificity of an antibody of claim 2 which is a humanized antibody.

27. An antibody having the binding specificity of an antibody of claim 2 which is a human antibody.

* * * * *

SEQUENCE LISTING

```
<160> NUMBER OF SEQ ID NOS: 4

<210> SEQ ID NO 1
<211> LENGTH: 5484
<212> TYPE: DNA
<213> ORGANISM: Homo sapiens

<400> SEQUENCE: 1
aattgtcagc acgggatctg agacttccaa aaaatgaagc cggcgacagg actttgggtc      60
```

```
tgggtgagcc ttctcgtggc ggcggggacc gtccagccca gcgattctca gtcagtgtgt    120
gcaggaacgg agaataaact gagctctctc tctgacctgg aacagcagta ccgagccttg    180
cgcaagtact atgaaaactg tgaggttgtc atgggcaacc tggagataac cagcattgag    240
cacaaccggg acctctcctt cctgcggtct gttcgagaag tcacaggcta cgtgttagtg    300
gctcttaatc agtttcgtta cctgcctctg gagaatttac gcattattcg tgggacaaaa    360
ctttatgagg atcgatatgc cttggcaata ttttaaact acagaaaaga tggaaacttt     420
ggacttcaag aacttggatt aaagaacttg acagaaatcc taaatggtgg agtctatgta    480
gaccagaaca aattcctttg ttatgcagac accattcatt ggcaagatat tgttcggaac    540
ccatggcctt ccaacttgac tcttgtgtca acaaatggta gttcaggatg tggacgttgc    600
cataagtcct gtactggccg ttgctgggga cccacagaaa atcattgcca gactttgaca    660
aggacggtgt gtgcagaaca atgtgacggc agatgctacg gaccttacgt cagtgactgc    720
tgccatcgag aatgtgctgg aggctgctca ggacctaagg acacagactg ctttgcctgc    780
atgaatttca tgacagtgga agcatgtgtt actcagtgtc cccaaacctt tgtctacaat    840
ccaaccacct ttcaactgga gcacaatttc aatgcaaagt acacatatgg agcattctgt    900
gtcaagaaat gtccacataa ctttgtggta gattccagtt cttgtgtgcg tgcctgccct    960
agttccaaga tggaagtaga agaaaatggg attaaaatgt gtaaaccttg cactgacatt   1020
tgcccaaaag cttgtgatgg cattggcaca ggatcattga tgtcagctca gactgtggat   1080
tccagtaaca ttgacaaatt cataaactgt accaagatca atgggaattt gatctttcta   1140
gtcactggta ttcatgggga cccttacaat gcaattgaag ccatagaccc agagaaactg   1200
aacgtctttc ggacagtcag agagataaca ggtttcctga acatacagtc atggccacca   1260
aacatgactg acttcagtgt tttttctaac ctggtgacca ttggtggaag agtactctat   1320
agtggcctgt ccttgcttat cctcaagcaa cagggcatca cctctctaca gttccagtcc   1380
ctgaaggaaa tcagcgcagg aaacatctat attactgaca acagcaacct gtgttattat   1440
cataccatta actggacaac actcttcagc acaatcaacc agagaatagt aatccgggac   1500
aacagaaaag ctgaaaattg tactgctgaa ggaatggtgt gcaaccatct gtgttccagt   1560
gatggctgtt ggggacctgg gccagaccaa tgtctgtcgt gtcgccgctt cagtagagga   1620
aggatctgca tagagtcttg taacctctat gatggtgaat tcgggagtt tgagaatggc    1680 tccatctgtg tggagtgtga cccccagtgt gagaagatgg aagatggcct cctcacatgc   1740 catgaccgg gtcctgacaa ctgtacaaag tgctctcatt ttaaagatgg cccaaactgt    1800
gtggaaaaat gtccagatgg cttacagggg gcaaacagtt tcattttcaa gtatgctgat    1860
ccagatcggg agtgccaccc atgccatcca aactgcaccc aagggtgtaa cggtcccact   1920
agtcatgact gcatttacta cccatggacg ggccattcca ctttaccaca acatgctaga    1980
actcccctga ttgcagctgg agtaattggt gggctcttca ttctggtcat tgtgggtctg    2040
acatttgctg tttatgttag aaggaagagc atcaaaaaga aaagagcctt gagaagattc    2100
ttggaaacag agttggtgga accattaact cccagtggca cagcacccaa tcaagctcaa    2160 cttcgtatt tgaaagaaac tgagctgaag agggtaaaag tccttggctc aggtgctttt    2220
ggaacggttt ataaggtat tgggtacct gaaggagaaa ctgtgaagat tcctgtggct    2280
attaagattc ttaatgagac aactggtccc aaggcaaatg tggagttcat ggatgaagct    2340
ctgatcatgg caagtatgga tcatccacac ctagtccggt tgctgggtgt gtgtctgagc    2400
ccaaccatcc agctggttac tcaacttatg ccccatggct gcctgttgga gtatgtccac    2460
```

```
gagcacaagg ataacattgg atcacaactg ctgcttaact ggtgtgtcca gatagctaag      2520
ggaatgatgt acctggaaga aagacgactc gttcatcggg atttggcagc ccgtaatgtc      2580
ttagtgaaat ctccaaacca tgtgaaaatc acagattttg ggctagccag actcttggaa      2640
ggagatgaaa aagagtacaa tgctgatgga ggaaagatgc aattaaatg gatggctctg       2700 gagtgtatac attacaggaa attcacccat cagagtgacg tttggagcta tggagttact      2760
atatgggaac tgatgacctt tggaggaaaa ccctatgatg aattccaac gcgagaaatc       2820 cctgatttat tagagaaagg agaacgtttg cctcagcctc ccatctgcac tattgacgtt      2880
tacatggtca tggtcaaatg ttggatgatt gatgctgaca gtagacctaa atttaaggaa      2940
ctggctgctg agttttcaag gatggctcga gaccctcaaa gatacctagt tattcagggt      3000
gatgatcgta tgaagcttcc cagtccaaat gacagcaagt tctttcagaa tctcttggat      3060
gaagaggatt tggaagatat gatggatgct gaggagtact tggtccctca ggctttcaac      3120
atcccacctc ccatctatac ttccagagca agaattgact cgaataggag tgaaattgga      3180
cacagccctc ctcctgccta cacccccatg tcaggaaacc agtttgtata ccgagatgga      3240
ggttttgctg ctgaacaagg agtgtctgtg ccctacagag ccccaactag cacaattcca      3300
gaagctcctg tggcacaggg tgctactgct gagattttg atgactcctg ctgtaatggc       3360
accctacgca agccagtggc accccatgtc caagaggaca gtagcaccca gaggtacagt      3420
gctgacccca ccgtgtttgc cccagaacgg agcccacgag gagagctgga tgaggaaggt      3480
tacatgactc ctatgcgaga caaacccaaa caagaatacc tgaatccagt ggaggagaac      3540
ccttttgttt ctcggagaaa aaatggagac cttcaagcat tggataatcc cgaatatcac      3600
aatgcatcca atggtccacc caaggccgag gatgagtatg tgaatgagcc actgtacctc      3660 aacaccttg ccaacacctt gggaaaagct gagtacctga agaacaacat actgtcaatg      3720
ccagagaagg ccaagaaagc gtttgacaac cctgactact ggaaccacag cctgccacct      3780
cggagcaccc ttcagcaccc agactacctg caggagtaca gcacaaaata ttttatataaa      3840 cagaatgggc ggatccggcc tattgtggca gagaatcctg aatacctctc tgagttctcc      3900
ctgaagccag gcactgtgct gccgcctcca ccttacagac accggaatac tgtggtgtaa      3960
gctcagttgt ggtttttag gtggagagac acacctgctc caatttcccc accccctct        4020 cttttctctgg tggtcttcct tctacccccaa ggccagtagt tttgacactt cccagtggaa      4080
gatacagaga tgcaatgata gttatgtgct tacctaactt gaacattaga gggaaagact      4140
gaaagagaaa gataggagga accacaatgt ttcttcattt ctctgcatgg gttggtcagg      4200
agaatgaaac agctagagaa ggaccagaaa atgtaaggca atgctgccta ctatcaaact      4260
agctgtcact tttttttcttt ttcttttttct ttctttgttt ctttcttcct cttcttttt       4320 ttttttttt taaagcagat ggttgaaaca cccatgctat ctgttcctat ctgcaggaac       4380
tgatgtgtgc atatttagca tccctggaaa tcataataaa gtttccatta gaacaaaaga      4440
ataacatttt ctataacata tgatagtgtc tgaaattgag aatccagttt ctttccccag      4500
cagtttctgt cctagcaagt aagaatggcc aactcaactt tcataattta aaaatctcca      4560
ttaaagttat aactagtaat tatgttttca acacttttg gtttttttca ttttgttttg      4620
ctctgaccga ttcctttata tttgctcccc tattttggc tttaatttct aattgcaaag      4680
atgtttacat caaagcttct tcacagaatt taagcaagaa atattttaat atagtgaaat      4740
ggccactact ttaagtatac aatctttaaa ataagaaagg gaggctaata tttttcatgc      4800
```

-continued

```
tatcaaatta tcttcaccct catcctttac attttttcaac attttttttt ctccataaat     4860
gacactactt gataggccgt tggttgtctg aagagtagaa gggaaactaa gagacagttc     4920
tctgtggttc aggaaaacta ctgatacttt caggggtggc ccaatgaggg aatccattga     4980
actggaagaa acacactgga ttgggtatgt ctacctggca gatactcaga aatgtagttt     5040
gcacttaagc tgtaatttta tttgttcttt ttctgaactc cattttggat tttgaatcaa     5100
gcaatatgga agcaaccagc aaattaacta atttaagtac attttaaaaa aaagagctaa     5160
gataaagact gtggaaatgc caaaccaagc aaattaggaa ccttgcaacg gtatccaggg     5220
actatgatga gaggccagca cattatcttc atatgtcacc tttgctacgc aaggaaattt     5280
gttcagttcg tatacttcgt aagaaggaat gcgagtaagg attggcttga attccatgga     5340
atttctagta tgagactatt tatatgaagt agaaggtaac tctttgcaca taaattggta     5400
taataaaaag aaaaacacaa acattcaaag cttagggata ggtccttggg tcaaaagttg     5460
taaataaatg tgaaacatct tctc                                           5484
```

<210> SEQ ID NO 2
<211> LENGTH: 1308
<212> TYPE: PRT
<213> ORGANISM: Homo sapiens

<400> SEQUENCE: 2

```
Met Lys Pro Ala Thr Gly Leu Trp Val Trp Val Ser Leu Leu Val Ala
 1               5                  10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45

Leu Arg Lys Tyr Tyr Glu Asn Cys Glu Val Val Met Gly Asn Leu Glu
    50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255
```

-continued

```
Ala Cys Val Thr Gln Cys Pro Gln Thr Phe Val Tyr Asn Pro Thr Thr
            260                 265                 270
Phe Gln Leu Glu His Asn Phe Asn Ala Lys Tyr Thr Tyr Gly Ala Phe
        275                 280                 285
Cys Val Lys Lys Cys Pro His Asn Phe Val Val Asp Ser Ser Ser Cys
    290                 295                 300
Val Arg Ala Cys Pro Ser Ser Lys Met Glu Val Glu Glu Asn Gly Ile
305                 310                 315                 320
Lys Met Cys Lys Pro Cys Thr Asp Ile Cys Pro Lys Ala Cys Asp Gly
                325                 330                 335
Ile Gly Thr Gly Ser Leu Met Ser Ala Gln Thr Val Asp Ser Ser Asn
            340                 345                 350
Ile Asp Lys Phe Ile Asn Cys Thr Lys Ile Asn Gly Asn Leu Ile Phe
        355                 360                 365
Leu Val Thr Gly Ile His Gly Asp Pro Tyr Asn Ala Ile Glu Ala Ile
    370                 375                 380
Asp Pro Glu Lys Leu Asn Val Phe Arg Thr Val Arg Glu Ile Thr Gly
385                 390                 395                 400
Phe Leu Asn Ile Gln Ser Trp Pro Pro Asn Met Thr Asp Phe Ser Val
                405                 410                 415
Phe Ser Asn Leu Val Thr Ile Gly Gly Arg Val Leu Tyr Ser Gly Leu
            420                 425                 430
Ser Leu Leu Ile Leu Lys Gln Gln Gly Ile Thr Ser Leu Gln Phe Gln
        435                 440                 445
Ser Leu Lys Glu Ile Ser Ala Gly Asn Ile Tyr Ile Thr Asp Asn Ser
    450                 455                 460
Asn Leu Cys Tyr Tyr His Thr Ile Asn Trp Thr Thr Leu Phe Ser Thr
465                 470                 475                 480
Ile Asn Gln Arg Ile Val Ile Arg Asp Asn Arg Lys Ala Glu Asn Cys
                485                 490                 495
Thr Ala Glu Gly Met Val Cys Asn His Leu Cys Ser Ser Asp Gly Cys
            500                 505                 510
Trp Gly Pro Gly Pro Asp Gln Cys Leu Ser Cys Arg Arg Phe Ser Arg
        515                 520                 525
Gly Arg Ile Cys Ile Glu Ser Cys Asn Leu Tyr Asp Gly Glu Phe Arg
    530                 535                 540
Glu Phe Glu Asn Gly Ser Ile Cys Val Glu Cys Asp Pro Gln Cys Glu
545                 550                 555                 560
Lys Met Glu Asp Gly Leu Leu Thr Cys His Gly Pro Gly Pro Asp Asn
                565                 570                 575
Cys Thr Lys Cys Ser His Phe Lys Asp Gly Pro Asn Cys Val Glu Lys
            580                 585                 590
Cys Pro Asp Gly Leu Gln Gly Ala Asn Ser Phe Ile Phe Lys Tyr Ala
        595                 600                 605
Asp Pro Asp Arg Glu Cys His Pro Cys His Pro Asn Cys Thr Gln Gly
    610                 615                 620
Cys Asn Gly Pro Thr Ser His Asp Cys Ile Tyr Tyr Pro Trp Thr Gly
625                 630                 635                 640
His Ser Thr Leu Pro Gln His Ala Arg Thr Pro Leu Ile Ala Ala Gly
                645                 650                 655
Val Ile Gly Gly Leu Phe Ile Leu Val Ile Val Gly Leu Thr Phe Ala
            660                 665                 670
```

-continued

```
Val Tyr Val Arg Arg Lys Ser Ile Lys Lys Arg Ala Leu Arg Arg
        675                 680                 685

Phe Leu Glu Thr Glu Leu Val Glu Pro Leu Thr Pro Ser Gly Thr Ala
    690                 695                 700

Pro Asn Gln Ala Gln Leu Arg Ile Leu Lys Thr Glu Leu Lys Arg
705                 710                 715                 720

Val Lys Val Leu Gly Ser Gly Ala Phe Gly Thr Val Tyr Lys Gly Ile
                725                 730                 735

Trp Val Pro Glu Gly Glu Thr Val Lys Ile Pro Val Ala Ile Lys Ile
            740                 745                 750

Leu Asn Glu Thr Thr Gly Pro Lys Ala Asn Val Glu Phe Met Asp Glu
        755                 760                 765

Ala Leu Ile Met Ala Ser Met Asp His Pro His Leu Val Arg Leu Leu
    770                 775                 780

Gly Val Cys Leu Ser Pro Thr Ile Gln Leu Val Thr Gln Leu Met Pro
785                 790                 795                 800

His Gly Cys Leu Leu Glu Tyr Val His Glu His Lys Asp Asn Ile Gly
                805                 810                 815

Ser Gln Leu Leu Leu Asn Trp Cys Val Gln Ile Ala Lys Gly Met Met
            820                 825                 830

Tyr Leu Glu Glu Arg Arg Leu Val His Arg Asp Leu Ala Ala Arg Asn
        835                 840                 845

Val Leu Val Lys Ser Pro Asn His Val Lys Ile Thr Asp Phe Gly Leu
    850                 855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
                885                 890                 895

Phe Thr His Gln Ser Asp Val Trp Ser Tyr Gly Val Thr Ile Trp Glu
            900                 905                 910

Leu Met Thr Phe Gly Gly Lys Pro Tyr Asp Gly Ile Pro Thr Arg Glu
        915                 920                 925

Ile Pro Asp Leu Leu Glu Lys Gly Glu Arg Leu Pro Gln Pro Pro Ile
    930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
                965                 970                 975

Met Ala Arg Asp Pro Gln Arg Tyr Leu Val Ile Gln Gly Asp Asp Arg
            980                 985                 990

Met Lys Leu Pro Ser Pro Asn Asp Ser Lys Phe Phe Gln Asn Leu Leu
        995                 1000                1005

Asp Glu Glu Asp Leu Glu Asp Met Met Asp Ala Glu Glu Tyr Leu Val
    1010                1015                1020

Pro Gln Ala Phe Asn Ile Pro Pro Pro Ile Tyr Thr Ser Arg Ala Arg
1025                1030                1035                1040

Ile Asp Ser Asn Arg Ser Glu Ile Gly His Ser Pro Pro Pro Ala Tyr
                1045                1050                1055

Thr Pro Met Ser Gly Asn Gln Phe Val Tyr Arg Asp Gly Gly Phe Ala
            1060                1065                1070

Ala Glu Gln Gly Val Ser Val Pro Tyr Arg Ala Pro Thr Ser Thr Ile
        1075                1080                1085

Pro Glu Ala Pro Val Ala Gln Gly Ala Thr Ala Glu Ile Phe Asp Asp
```

```
              1090                1095                1100
Ser Cys Cys Asn Gly Thr Leu Arg Lys Pro Val Ala Pro His Val Gln
1105                1110                1115                1120

Glu Asp Ser Ser Thr Gln Arg Tyr Ser Ala Asp Pro Thr Val Phe Ala
                1125                1130                1135

Pro Glu Arg Ser Pro Arg Gly Glu Leu Asp Glu Glu Gly Tyr Met Thr
            1140                1145                1150

Pro Met Arg Asp Lys Pro Lys Gln Glu Tyr Leu Asn Pro Val Glu Glu
            1155                1160                1165

Asn Pro Phe Val Ser Arg Arg Lys Asn Gly Asp Leu Gln Ala Leu Asp
        1170                1175                1180

Asn Pro Glu Tyr His Asn Ala Ser Asn Gly Pro Pro Lys Ala Glu Asp
1185                1190                1195                1200

Glu Tyr Val Asn Glu Pro Leu Tyr Leu Asn Thr Phe Ala Asn Thr Leu
                1205                1210                1215

Gly Lys Ala Glu Tyr Leu Lys Asn Asn Ile Leu Ser Met Pro Glu Lys
            1220                1225                1230

Ala Lys Lys Ala Phe Asp Asn Pro Asp Tyr Trp Asn His Ser Leu Pro
            1235                1240                1245

Pro Arg Ser Thr Leu Gln His Pro Asp Tyr Leu Gln Glu Tyr Ser Thr
        1250                1255                1260

Lys Tyr Phe Tyr Lys Gln Asn Gly Arg Ile Arg Pro Ile Val Ala Glu
1265                1270                1275                1280

Asn Pro Glu Tyr Leu Ser Glu Phe Ser Leu Lys Pro Gly Thr Val Leu
                1285                1290                1295

Pro Pro Pro Pro Tyr Arg His Arg Asn Thr Val Val
            1300                1305

<210> SEQ ID NO 3
<211> LENGTH: 2601
<212> TYPE: DNA
<213> ORGANISM: Homo sapiens

<400> SEQUENCE: 3
ccaatcgatt tcgcggcaaa gaccttccgg tcctggacca gctgctcgag cagtcagtgt    60
gtgcaggaac ggagaataaa ctgagctctc tctctgacct ggaacagcag taccgagcct   120
tgcgcaagta ctatgaaaac tgtgaggttg tcatgggcaa cctggagata accagcattg   180
agcacaaccg ggacctctcc ttcctgcggt ctgttcgaga agtcacaggc tacgtgttag   240
tggctcttaa tcagtttcgt tacctgcctc tggagaattt acgcattatt cgtgggacaa   300
aactttatga ggatcgatat gccttggcaa tatttttaaa ctacagaaaa gatgaaaact   360
ttggacttca agaacttgga ttaaagaact tgacagaaat cctaaatggt ggagtctatg   420
tagaccagaa caaattcctt tgttatgcag acaccattca ttggcaagat attgttcgga   480
acccatggcc ttccaacttg actcttgtgt caacaaatgg tagttcagga tgtggacgtt   540
gccataagtc ctgtactggc cgttgctggg accccacaga aaatcattgc cagactttga   600
caaggacggt gtgtgcagaa caatgtgacg gcagatgcta cggaccttac gtcagtgact   660
gctgccatcg agaatgtgct ggaggctgct caggacctaa ggacacagac tgctttgcct   720
gcatgaattt caatgacagt ggagcatgtg ttactcagtg tccccaaacc tttgtctaca   780
atccaaccac ctttcaactg gagcacaatt tcaatgcaaa gtacacatat ggagcattct   840
gtgtcaagaa atgtccacat aactttgtgg tagattccag ttcttgtgtg cgtgcctgcc   900
```

-continued

```
ctagttccaa gatggaagta aagaaaatg ggattaaaat gtgtaaacct tgcactgaca      960
tttgcccaaa agcttgtgat ggcattggca caggatcatt gatgtcagct cagactgtgg    1020
attccagtaa cattgacaaa ttcataaact gtaccaagat caatgggaat ttgatctttc    1080
tagtcactgg tattcatggg gacccttaca atgcaattga agccatagac ccagagaaac    1140
tgaacgtctt tcggacagtc agagagataa caggtttcct gaacatacag tcatggccac    1200
caaacatgac tgacttcagt gttttttcta acctggtgac cattggtgga agagtactct    1260
atagtggcct gtccttgctt atcctcaagc aacagggcat cacctctcta cagttccagt    1320
ccctgaagga aatcagcgca ggaaacatct atattactga acagcaaac ctgtgttatt    1380
atcataccat taactggaca acactcttca gcacaatcaa ccagagaata gtaatccggg    1440
acaacagaaa agctgaaaat tgtactgctg aaggaatggt gtgcaaccat ctgtgttcca    1500
gtgatggctg ttgggggacct gggccagacc aatgtctgtc gtgtcgccgc ttcagtagag    1560
gaaggatctg catagagtct tgtaacctct atgatggtga atttcgggag tttgagaatg    1620
gctccatctg tgtggagtgt gacccccagt gtgagaagat ggaagatggc ctcctcacat    1680
gccatggacc gggtcctgac aactgtacaa agtgctctca tttttaaagat ggcccaaact    1740
gtgtggaaaa atgtccagat ggcttacagg gggcaaacag tttcattttc aagtatgctg    1800
atccagatcg ggagtgccac ccatgccatc caaactgcac ccaagggtgt aacggtccca    1860
ctagtcatga ctgcattac tacccatgga cgggcacgcg tgacaaaact cacacatgcc    1920
caccgtgccc agcacctgaa ctcctggggg gaccgtcagt cttcctcttc ccccaaaac    1980
ccaaggacac cctcatgatc tcccggaccc ctgaggtcac atgcgtggtg gtggacgtga    2040
gccacgaaga ccctgaggtc aagttcaact ggtacgtgga cggcgtggag gtgcataatg    2100
ccaagacaaa gccgcgggag gagcagtaca acagcacgta ccgggtggtc agcgtcctca    2160
ccgtcctgca ccaggactgg ctgaatggca aggagtacaa gtgcaaggtc tccaacaaag    2220
ccctcccagc ccccatcgag aaaaccatct ccaaagccaa agggcagccc cgagaaccac    2280
aggtgtacac cctgccccca tcccgggaag agatgaccaa gaaccaggtc agcctgacct    2340
gcctggtcaa aggcttctat cccagcgaca tcgccgtgga gtgggagagc aatgggcagc    2400
cggagaacaa ctggcccacc cccttggctt acaagaccac gcctcccgtg ctggactccg    2460
acggctcctt cttcctctac agcaagctca ccgtggacaa gagcaggtgg cagcagggga    2520
acgtcttctc atgctccgtg atgcatgagg ctctgcacaa ccactacacg cagaagagcc    2580
tctccctgtc tccgggtaaa t                                               2601
```

<210> SEQ ID NO 4
<211> LENGTH: 615
<212> TYPE: PRT
<213> ORGANISM: Homo sapiens

<400> SEQUENCE: 4

```
Gln Ser Val Cys Ala Gly Thr Glu Asn Lys Leu Ser Ser Leu Ser Asp
  1               5                  10                  15

Leu Glu Gln Gln Tyr Arg Ala Leu Arg Lys Tyr Tyr Glu Asn Cys Glu
             20                  25                  30

Val Val Met Gly Asn Leu Glu Ile Thr Ser Ile Glu His Asn Arg Asp
         35                  40                  45

Leu Ser Phe Leu Arg Ser Val Arg Glu Val Thr Gly Tyr Val Leu Val
     50                  55                  60

Ala Leu Asn Gln Phe Arg Tyr Leu Pro Leu Glu Asn Leu Arg Ile Ile
```

-continued

```
              65                  70                  75                  80
         Arg Gly Thr Lys Leu Tyr Glu Asp Arg Tyr Ala Leu Ala Ile Phe Leu
                         85                  90                  95
         Asn Tyr Arg Lys Asp Gly Asn Phe Gly Leu Gln Glu Leu Gly Leu Lys
                        100                 105                 110
         Asn Leu Thr Glu Ile Leu Asn Gly Gly Val Tyr Val Asp Gln Asn Lys
                        115                 120                 125
         Phe Leu Cys Tyr Ala Asp Thr Ile His Trp Gln Asp Ile Val Arg Asn
             130                 135                 140
         Pro Trp Pro Ser Asn Leu Thr Leu Val Ser Thr Asn Gly Ser Ser Gly
         145                 150                 155                 160
         Cys Gly Arg Cys His Lys Ser Cys Thr Gly Arg Cys Trp Gly Pro Thr
                         165                 170                 175
         Glu Asn His Cys Gln Thr Leu Thr Arg Thr Val Cys Ala Glu Gln Cys
                         180                 185                 190
         Asp Gly Arg Cys Tyr Gly Pro Tyr Val Ser Asp Cys Cys His Arg Glu
                         195                 200                 205
         Cys Ala Gly Gly Cys Ser Gly Pro Lys Asp Thr Asp Cys Phe Ala Cys
             210                 215                 220
         Met Asn Phe Asn Asp Ser Gly Ala Cys Val Thr Gln Cys Pro Gln Thr
         225                 230                 235                 240
         Phe Val Tyr Asn Pro Thr Thr Phe Gln Leu Glu His Asn Phe Asn Ala
                         245                 250                 255
         Lys Tyr Thr Tyr Gly Ala Phe Cys Val Lys Cys Pro His Asn Phe
                         260                 265                 270
         Val Val Asp Ser Ser Ser Cys Val Arg Ala Cys Pro Ser Ser Lys Met
                         275                 280                 285
         Glu Val Glu Glu Asn Gly Ile Lys Met Cys Lys Pro Cys Thr Asp Ile
                         290                 295                 300
         Cys Pro Lys Ala Cys Asp Gly Ile Gly Thr Gly Ser Leu Met Ser Ala
         305                 310                 315                 320
         Gln Thr Val Asp Ser Ser Asn Ile Asp Lys Phe Ile Asn Cys Thr Lys
                         325                 330                 335
         Ile Asn Gly Asn Leu Ile Phe Leu Val Thr Gly Ile His Gly Asp Pro
                         340                 345                 350
         Tyr Asn Ala Ile Glu Ala Ile Asp Pro Glu Lys Leu Asn Val Phe Arg
                         355                 360                 365
         Thr Val Arg Glu Ile Thr Gly Phe Leu Asn Ile Gln Ser Trp Pro Pro
                         370                 375                 380
         Asn Met Thr Asp Phe Ser Val Phe Ser Asn Leu Val Thr Ile Gly Gly
         385                 390                 395                 400
         Arg Val Leu Tyr Ser Gly Leu Ser Leu Leu Ile Leu Lys Gln Gln Gly
                         405                 410                 415
         Ile Thr Ser Leu Gln Phe Gln Ser Leu Lys Glu Ile Ser Ala Gly Asn
                         420                 425                 430
         Ile Tyr Ile Thr Asp Asn Ser Asn Leu Cys Tyr Tyr His Thr Ile Asn
                         435                 440                 445
         Trp Thr Thr Leu Phe Ser Thr Ile Asn Gln Arg Ile Val Ile Arg Asp
                         450                 455                 460
         Asn Arg Lys Ala Glu Asn Cys Thr Ala Glu Gly Met Val Cys Asn His
         465                 470                 475                 480
         Leu Cys Ser Ser Asp Gly Cys Trp Gly Pro Gly Pro Asp Gln Cys Leu
                         485                 490                 495
```

-continued

```
Ser Cys Arg Arg Phe Ser Arg Gly Arg Ile Cys Ile Glu Ser Cys Asn
        500                 505                 510

Leu Tyr Asp Gly Glu Phe Arg Glu Phe Glu Asn Gly Ser Ile Cys Val
        515                 520                 525

Glu Cys Asp Pro Gln Cys Glu Lys Met Glu Asp Gly Leu Leu Thr Cys
        530                 535                 540

His Gly Pro Gly Pro Asp Asn Cys Thr Lys Cys Ser His Phe Lys Asp
545                 550                 555                 560

Gly Pro Asn Cys Val Glu Lys Cys Pro Asp Gly Leu Gln Gly Ala Asn
                565                 570                 575

Ser Phe Ile Phe Lys Tyr Ala Asp Pro Asp Arg Glu Cys His Pro Cys
                580                 585                 590

His Pro Asn Cys Thr Gln Gly Cys Asn Gly Pro Thr Ser His Asp Cys
        595                 600                 605

Ile Tyr Tyr Pro Trp Thr Gly
        610             615
```